United States Patent [19]

Fujii et al.

[11] Patent Number: 4,570,006

[45] Date of Patent: * Feb. 11, 1986

[54] AMIDINE COMPOUND, PROCESS FOR PRODUCING SAME AND ANTI-COMPLEMENT AGENT COMPRISING SAME

[75] Inventors: Setsuro Fujii, Toyonaka; Takashi Yaegashi; Toyoo Nakayama, both of Funabashi; Yojiro Sakurai, Kamakura; Shigeki Nunomura, Chiba; Toshiyuki Okutome, Tokyo, all of Japan

[73] Assignee: Torii & Co. Ltd., Tokyo, Japan

[*] Notice: The portion of the term of this patent subsequent to Apr. 30, 2002 has been disclaimed.

[21] Appl. No.: 664,261

[22] Filed: Oct. 24, 1984

Related U.S. Application Data

[63] Continuation of Ser. No. 611,937, May 21, 1984, Pat. No. 4,514,416, which is a continuation of Ser. No. 350,963, Feb. 22, 1982, abandoned.

[30] Foreign Application Priority Data

Feb. 27, 1981 [JP] Japan .................................. 56-27974
Sep. 7, 1981 [JP] Japan .................................. 56-140650

[51] Int. Cl.$^4$ .................... C07C 119/00; A61K 31/22; A61K 31/235

[52] U.S. Cl. ...................................... 549/442; 560/75; 560/81; 514/466; 560/86; 560/104; 514/488; 560/105; 560/107; 514/522; 560/109; 560/115; 514/529; 560/122; 514/530; 560/123; 514/531; 560/124; 560/125; 514/533; 560/128; 514/534; 560/140; 514/535; 560/142; 514/540; 514/541; 514/542; 514/546; 514/549; 549/436; 260/465 D; 560/1; 560/9; 560/12; 560/16; 560/18; 560/20; 560/32; 560/34; 560/37; 560/48; 560/49; 560/51; 560/55; 560/61; 560/66; 560/72

[58] Field of Search ............... 560/1, 9, 18, 16, 20, 560/32, 34, 12, 37, 48, 49, 51, 55, 72, 75, 81, 86, 66, 104, 105, 107, 109, 115, 122, 123, 124, 125, 128, 140, 142; 260/465 D; 424/282, 304, 305, 308, 309, 310, 311, 315; 549/436, 442; 514/466, 488, 522, 529, 530, 531, 533, 534, 535, 540, 541, 542, 546, 549

[56] References Cited

U.S. PATENT DOCUMENTS

4,454,338  6/1984  Fujii .................................... 560/34

FOREIGN PATENT DOCUMENTS

89611  5/1972  German Democratic Rep. .
56-110664  9/1981  Japan .................................... 560/34

OTHER PUBLICATIONS

Fujii, Biochim. Biophys. Acta., 661 pp. 342–345 (10/31/81).

*Primary Examiner*—Michael L. Shippen
*Attorney, Agent, or Firm*—Beveridge, DeGrandi and Weilacher

[57] ABSTRACT

Amidino compounds represented by the formula

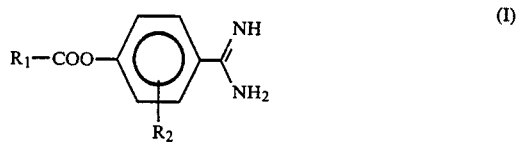
(I)

and pharmaceutically acceptable acid addition salts thereof are novel compounds and are useful as powerful anti-trypsine, anti-plasmin, anti-kallikrein and anti-thrombin agents. Having strong anti-Cl (C$\overline{1r}$, C$\overline{1s}$) activities and an anticomplement activity, they are also useful as anticomplement agents. These amidino compounds are prepared by usual esterification of carboxylic acid compounds represented by the formula (II)

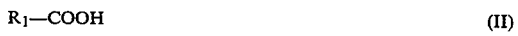

with amidinophenol compound (III) and, if necessary, can be transformed into pharmaceutically acceptable acid addition salts thereof.

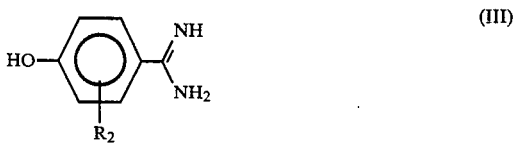

(III)

4 Claims, No Drawings

AMIDINE COMPOUND, PROCESS FOR PRODUCING SAME AND ANTI-COMPLEMENT AGENT COMPRISING SAME

This application is a continuation of application Ser. No. 611,937, filed May 21, 1984, now U.S. Pat. No. 4,514,416, which is a continuation of application Ser. No. 350,963, filed Feb. 22, 1982, now abandoned.

This invention relates to novel amidino compounds (I) of the formula

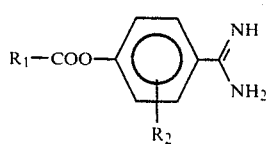

having strong anti-trypsin, anti-plasmin, anti-kallikrein and anti-thrombin activities and also an anti-complement activity, and to a process for producing said novel compounds.

The present compound (I) has anti-trypsin, anti-plasmin, anti-thrombin and anti-complement activities stronger than those of leupeptin. This means that with respect to anti-trypsin, anti-plasmin, anti-kallikrein, anti-thrombin and anti-complement activities, the same pharmaceutical effect is obtained with a smaller dose of the compound (I) than with a dose of leupeptin.

An object of this invention is to provide a pharmaceutically useful novel amidino compounds represented by the formula (I)

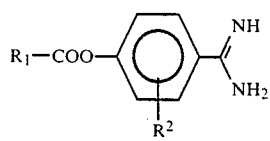

and pharmaceutically acceptable acid addition salts thereof.

Another object of this invention is to provide powerful anti-trypsin, anti-plasmin, anti-kallikrein and anti-thrombin agents.

A still another object of this invention is to provide powerful anti-complement agents.

A further object of this invention is to provide a process for producing said novel amidino compounds.

The present compound (I) can be produced by subjecting a carboxylic acid compound represented by the following formula (II) or a reactive intermediate thereof and amidino phenol compound of the following formula (III) to usual esterification:

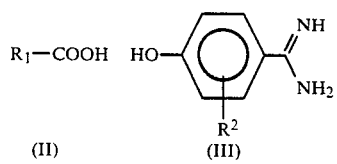

This invention relates to an amidino compound represented by the formula (I)

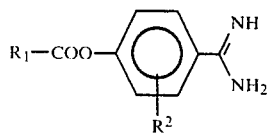

In formulas of the amidino compound (I), the carboxylic acid compound (II) and the amidino phenol compound (III) described in this specification and the appended claims, $R_1$ represents a straight or branched chain alkyl group of 1 to 6 carbon atoms, a straight or branched chain alkenyl group of 2 to 6 carbon atoms including 1 to 3 double bonds, $R_3$—$(CH_2)_a$—, $R_4$—$(CH_2)_b$—,

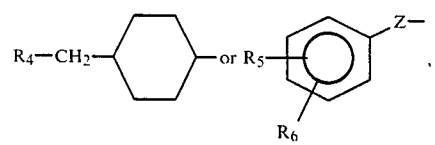

where $R_3$ is cycloalkyl group of 3 to 6 carbon atoms or cycloalkenyl group of 3 to 6 carbon atoms including 1 to 2 double bonds; a is 0, 1, 2 or 3; $R_4$ is amino or guanidino group possessing radical protecting group or not; b is a number of 1 to 5; $R_5$ and $R_6$, which may be the same or different, are each a hydrogen atom, straight or branched alkyl group of 1 to 4 carbon atoms, —$OR_7$, methylenedioxy group, —$SR_7$, —$COOR_7$, —$COR_8$, —$OCOR_9$, —$NHCOR_9$,

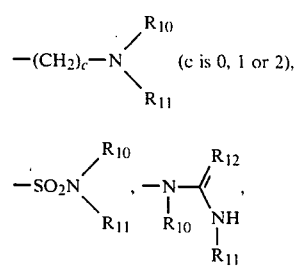

$NO_2$, CN, halogen atom, —$CF_3$ or

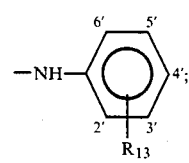

$R_7$ is hydrogen atom, straight or branched alkyl group of 1 to 4 carbon atoms or benzyl group; $R_8$ is hydrogen atom, straight or branched alkyl group of 1 to 4 carbon atoms; $R_9$ is straight or branched alkyl group of 1 to 4 carbon atoms; $R_{10}$ and $R_{11}$, which may be the same or different, are each a hydrogen atom, straight or branched alkyl group of 1 to 4 carbon atoms, or amino radical protecting group; $R_{12}$ is O, S, or NH; $R_{13}$ is 2', 3'-dimethyl or 3'-$CF_3$ group; Z is —$(CH_2)_d$— (d is 0, 1, 2 or 3),

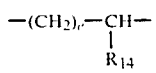

(e is 0, 1 or 2) or

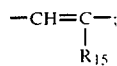

$R_{14}$ is straight or branched alkyl group of 1 to 4 carbon atoms; $R_{15}$ is hydrogen atom, straight or branched alkyl group of 1 to 4 carbon atoms; $R_2$ represents $-R_{16}$, $-OR_{16}$, $-COOR_{17}$, halogen atom, $-NO_2$, $-SO_3H$,

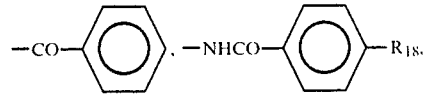

wherein $R_{16}$ is straight or branched alkyl group of 1 to 4 carbon atoms; $R_{17}$ is hydrogen atom, straight or branched alkyl group of 1 to 4 carbon atoms; $R_{18}$ is hydrogen atom or guanidino group.

In substituents $R_1$-$R_{14}$, straight or branched alkyl group of 1 to 4 carbon atoms include $CH_3$, $C_2H_5$, n-$C_3H_7$, i-$C_3H_7$, n-$C_4H_9$, i-$C_4H_9$, sec-$C_4H_9$, or t-$C_4H_9$, and examples of straight or branched alkyl group of 1 to 6 carbon atoms is $CH_3$, $C_2H_5$, n-$C_3H_7$, i-$C_3H_7$, n-$C_4H_9$, i-$C_4H_9$, sec-$C_4H_9$, t-$C_4H_9$, n-$C_5H_{11}$, or n-$C_6H_{13}$.

Straight or branched alkenyl group of 2 to 6 carbon atoms containing 1 to 3 double bonds include $CH_2=CH-$, $CH_3-CH=CH-$, $CH_2=CH-CH=CH-$, $CH_3-CH=CH-CH_2-$,

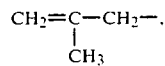

$CH_3-CH=CH-CH=CH-$,

or $CH_2=CH-CH=CH-CH=CH-$ as examples.

Cycloalkyl group of 3 to 6 carbon atoms or cycloalkenyl group of 3 to 6 carbon atoms containing 1 to 2 double bonds include

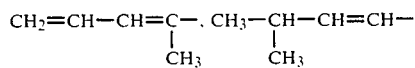

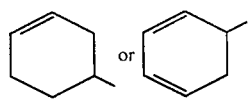

as examples.

Amino or guanidino radical protecting group include t-butoxycarbonyl, benzyloxycarbonyl, acetyl, benzoyl, tosyl or nitro as examples.

Then, $R_1$ represents following examples: $CH_3$, $C_2H_5$, n-$C_3H_7$, i-$C_3H_7$, n-$C_4H_9$, i-$C_4H_9$, sec-$C_4H_9$, t-$C_4H_9$, n-$C_5H_{11}$, n-$C_6H_{13}$, $CH_2=CH-$, $CH_3CH=CH-$, $CH_2=CH-CH=CH-$, $CH_3-CH=CH-CH_2-$,

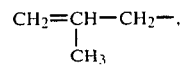

$CH_3CH=CH-CH=CH-$,

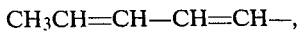

$CH_2=CH-CH=CH-CH=CH-$,

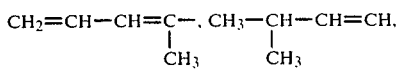

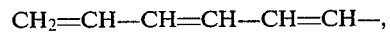

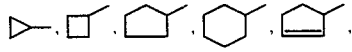

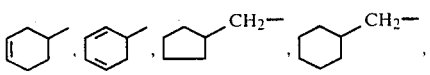

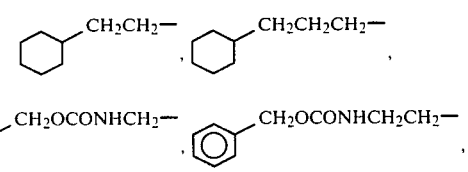

, $CH_3CONHCH_2-$,

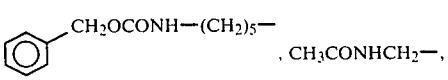

, $H_2NCH_2-$, $H_2NCH_2CH_2-$,

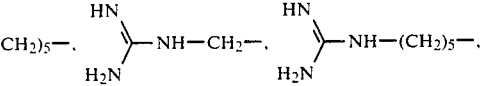

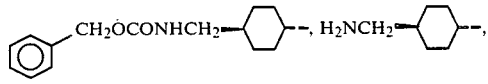

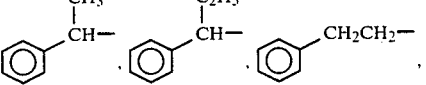

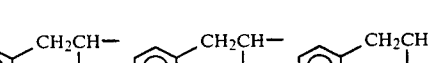

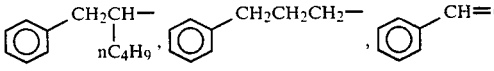

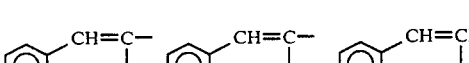

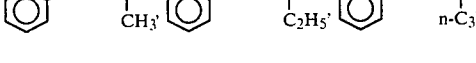

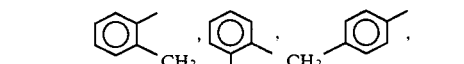

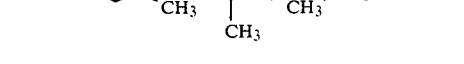

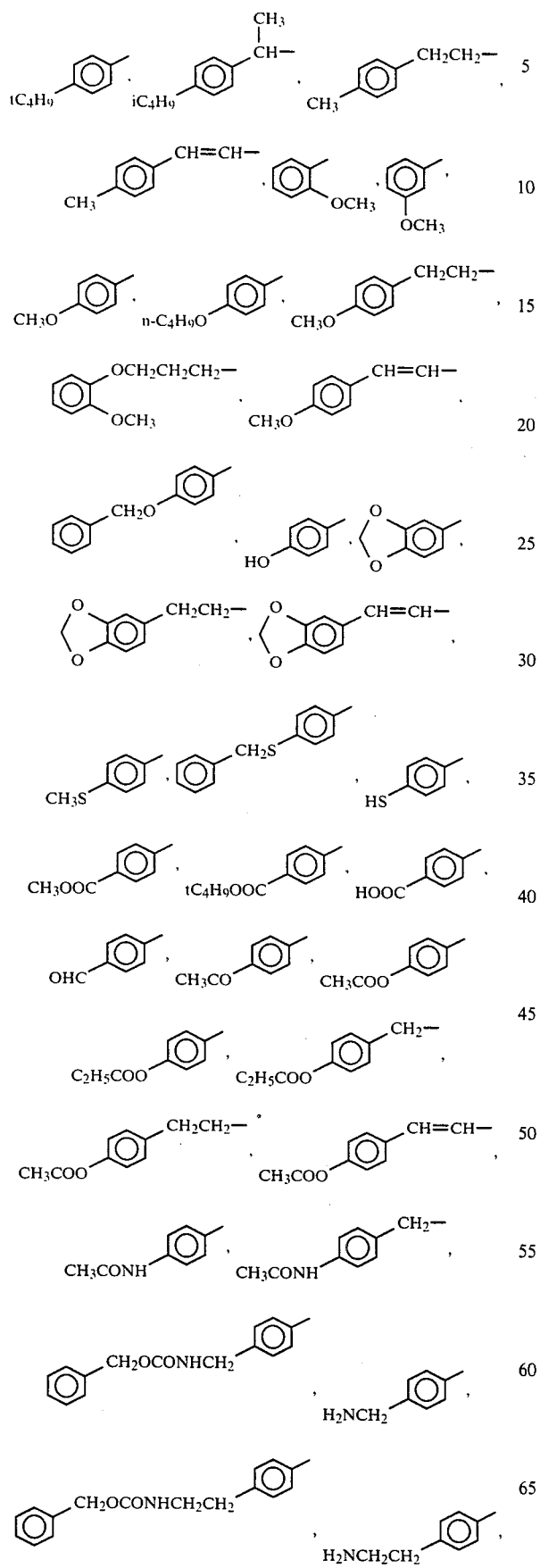
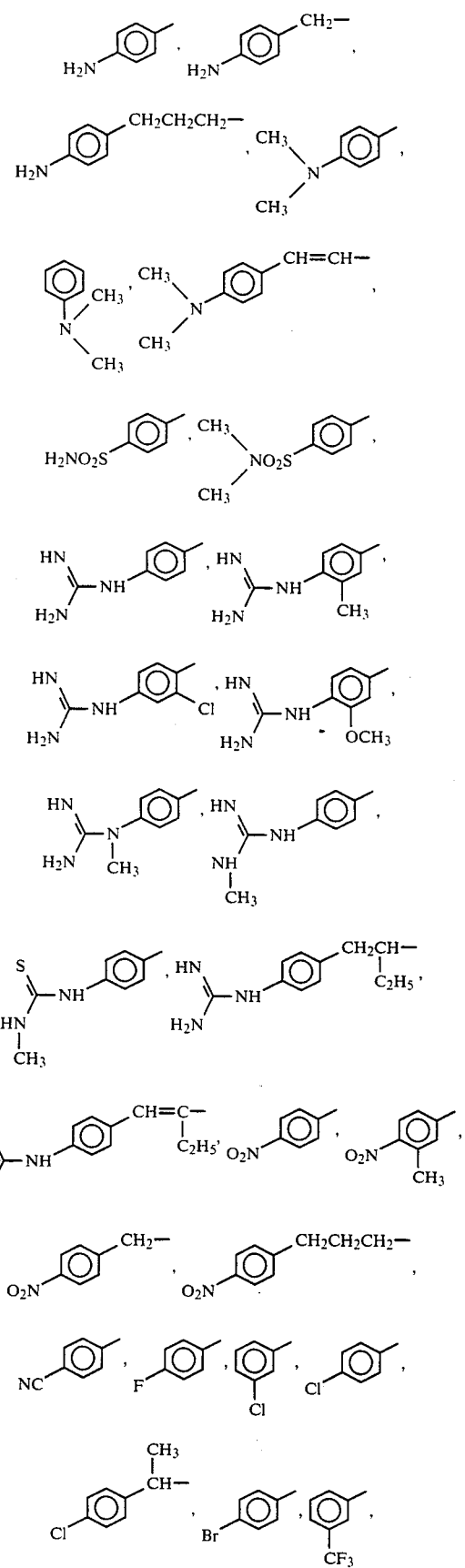

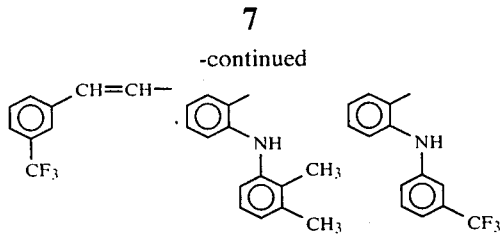

Amidinophenol moiety in amidino compound (I) or amidino phenol compound (III) include

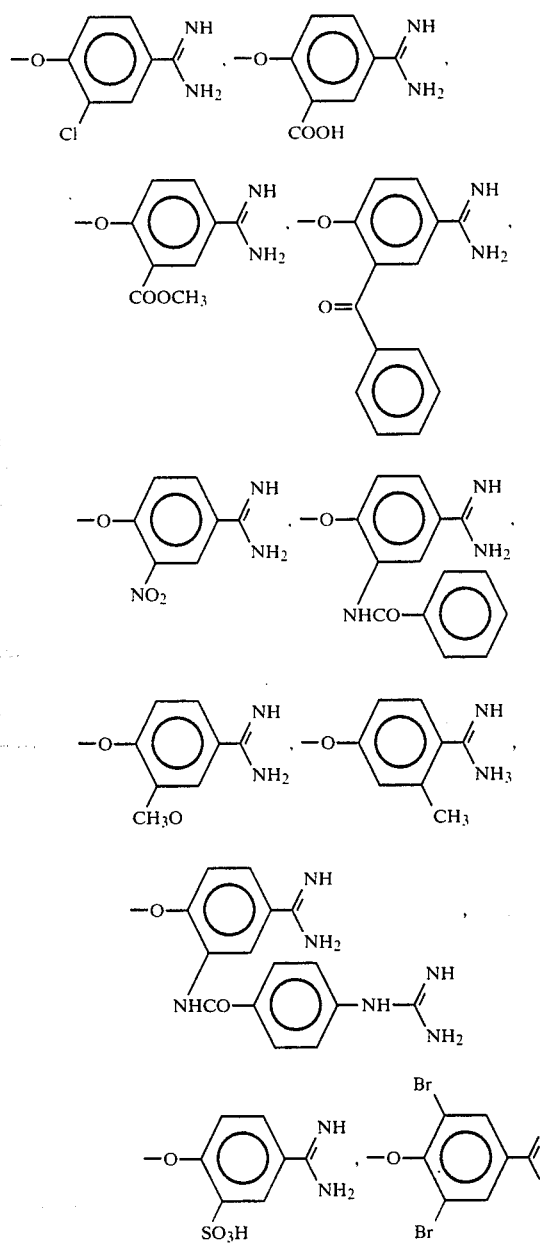

The compound (I) of this invention can be produced by the reaction between a carboxylic acid compound of the formula (II) or a reactive intermediate thereof and an amidinophenol compound of the formula (III) or preferably an acid addition salt thereof. The reactive intermediates, as herein referred to, include acid halides and acid anhydrides commonly used in the dehydration condensation and the reactive intermediates formed by reacting dicyclohexyl carbodiimide (DCC), diphenylphosphorylazide (DPPA), or the like with a carboxylic acid derivative.

The process for producing the present compound is described below in detail.

The present compound (I) can be prepared by dissolving or suspending a carboxylic acid compound (II) in an organic solvent such as dimethylformamide, pyridine, or the like, then allowing the compound (II) to react with an carboxylic acid activator such as dicyclohexylcarbodiimide (DCC), diphenylphosphoryl azide (DPPA), or the like, which is usually used as dehydration-condensation agent, and adding an amidinophenol compound (III) or preferably an acid addition salt thereof to the reaction product.

For instance, when DCC is used as the dehydration-condensation agent, a carboxylic acid derivative (II) is added to a solvent such as pyridine, then the mixture is stirred with cooling in ice or at room temperature for 10 minutes to 2 hours, then acid addition salt of amidine phenol compound (III) is added, and the mixture is further stirred at a temperature between −30° and 80° C., preferably at room temperature, for 3 to 5 hours to complete the reaction, though it is not objectionable to continue the reaction overnight. Dicyclohexylurea (DCU) precipitates out of the reaction mixture, while the present compound (I) either precipitates with DCU or remains dissolved in the solvent. In the former case, both precipitates are collected by filtration, then suspended in a suitable solvent such as dimethylformamide or the like and the mixture is filtered to remove insoluble DCU. After adding to the filtrate a solvent such as ethyl ether, ethyl acetate, acetone or the like, the precipitate is collected by filtration to obtain the present compound (I). Alternatively, the combined precipitate of DCU and the present compound (I) is collected by filtration, then added to a suitable solvent such as dimethylformamide, water or the like to remove insoluble DCU by filtration, the filtrate is added to a saturated aqueous sodium bicarbonate solution to obtain the present compound (I) in the form of carbonate. In the latter case, where the present compound remains dissolved in the reaction mixture, DCU is removed by filtration and the filtrate is admixed with a solvent such as ethyl ether, acetone, ethyl acetate, or the like to obtain the present compound (I).

In another process, when it is intended to use an acid halide as a reactive intermediate of a carboxylic acid derivative (II), the latter derivative (II) is allowed to react with an acidhalogenation agent such as $SOCl_2$, $SOBr_2$, $PCl_5$ or the like to synthesize an acid halide represented by the formula (IV)

$$R_1-COX \qquad (IV)$$

wherein $R_1$ is as defined above and X represents a halogen atom. The acid halide is added to a solution of an amidinophenol compound (III), preferably in the form of an acid addition salt, dissolved in dimethylformamide, pyridine, dimethyl sulfoxide or the like and allows to react in the presence of a dehydrohalogenation agent. The dehydrohalogenation agents which can be used include inorganic bases such as potassium carbonate, sodium carbonate, sodium hydroxide and the like and organic bases such as triethylamine, pyridine, dimethylaniline and the like. Of these bases, pyridine is preferred. Although the reaction proceeds readily at a temperature in the range of −30° to 80° C., it is preferable for the purpose of avoiding side reactions to conduct the reaction in the early stage under ice cooling and then at room temperature. The reaction is complete in 2 to 5 hours, though the reaction mixture can be left overnight.

The present compound (I) can be also prepared by which an acid halide (IV) and an amidinophenol compound are mixed, small amount of $CH_3SO_3H$ or $H_2SO_4$ is added therein and the mixture is warmed. After completion of the reaction, the reaction mixture is treated in a customary manner. For instance, when pyridine was used as the reaction medium, a solvent such as ethyl ether or ethyl acetate is added to the reaction mixture to precipitate a solid reaction product which is then recrystallized from a suitable solvent such as a methanol-ethyl ether mixture to obtain the present compound (I).

Further, if desired, the present compound (I) can be prepared in the corresponding reduced form by the reduction of a suitable compound of formula (I) by use of a suitable reducing agent. For example, a compound of formula (I) having a nitro group is converted into a compound of formula (I) having an amino group by the reduction. It is also possible to convert a cinnamic acid ester derivative having a double bond into a phenylpropionic acid derivative.

Still further, if desired, the present compound can be obtained by the removal of protective groups of amino, hydroxyl, and carboxyl groups. The protective groups, as herein referred to, include those which are commonly used, such as, for example, benzyloxycarbonyl, tert-butoxycarbonyl, benzyl and tert-butyl groups. For instance, a compound having an aminomethyl group is obtained by the removal of the protective group from a compound having a benzyloxycarbonylaminomethyl group and a compound having a hydroxyl group is obtained from a compound having a benzyloxy group.

If necessary, acid addition salts of the present compound may be prepared in a customary manner. For instance, carbonate of the present compound is dissolved or suspended in a solvent such as methanol, DMF or the like and the carbonate is allowed to dissolve by the addition of an acid such as methanesulfonic acid, hydrochloric acid or the like. To the resulting solution is added a solvent such as ethyl ether, ethyl acetate or the like to obtain a corresponding acid addition salt. Acids which can be used are pharmaceutically acceptable ones including inorganic acids such as hydrochloric acid, sulfuric acid and phosphoric acid and organic acids such as acetic acid, lactic acid, citric acid, methanesulfonic acid, succinic acid, fumaric acid and maleic acid.

Amidinophenol compound (III) is useful intermediate for preparation of the present compound (I). The amidinophenol compound (III) is prepared by various manner.

One is the method by introduction of substituent to amidinophenol (V), that is, introduction of $NO_2$ by $HNO_3/H_2SO_4$ ($R_2=2-NO_2$), of $SO_3H$ by $f-H_2SO_4$ ($R_2=2-SO_3H$), or of Br by $BR_2$ ($R_2=2, 6-diBr$) to amidinophenol (V) is one of examples.

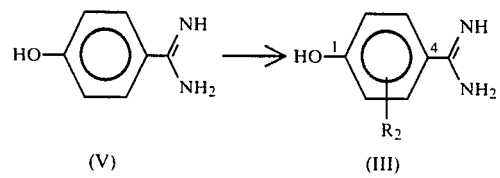

Another method is that nitril (VI) or amide (VII) of phenol is changed to iminoether (VIII) and then treated with ammonia to obtain amidinophenol compound (III) wherein A represent $CH_3$ or $C_2H_5$, B and X represent O or S. $R_2=3-CH_3$, $2-OCH_3$, $2-COOH$, $2-COOCH_3$, $-2-Cl$, or

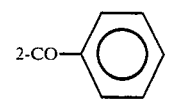

is example by the above mentioned method.

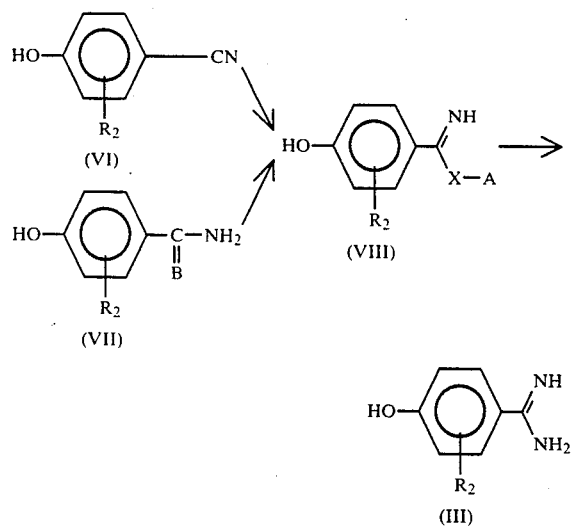

The present compound and the pharmaceutically acceptable acid addition salt thereof possess powerful inhibitory activities against proteases, that is, trypsin, plasmin, kallikrein and thrombin and are effective as an anti-trypsin agent for the treatment of pancreatitis, as an anti-plasmin or anti-kallikrein agent for hemorrhagic diseases, and as an anti-thrombin agent for thrombus.

With respect to the above-mentioned proteases, their roles in a living body, the relationship to the diseases, the clinical significance of these protease inhibitors and the significance of the tests herein performed are explained below:

I. Trypsin

Trypsin is a protease existing originally in the form of proenzyme trypsinogen in the pancreas and the proenzyme is secreted into the small intestine where it is transformed into trypsin by activation with enterokinase existing therein. Trypsin has a role as one of digestive enzymes. If the trypsinogen is activated by any chance in the pancreas to form trypsin, the pancreas tissue will be injured to manifest clinically the symptoms of pancreatitis. In fact, it is known that in an experiment using rat as test animal, when trypsin is injected conversely into the pancreas, the onset of intense pancreatitis is observed but the disease is cured by the administration of a trypsin inhibitor. From this fact, it is presumable that the present compound having a strong trypsin inhibitory activity is useful as an anti-trypsin agent which is clinically effective for the treatment of pancreatitis.

II. Plasmin

Plasmin is an enzyme existing in the blood, usually in the form of proenzyme plasminogen which is converted to plasmin by the activation with a plasminogen tissue activator such as urokinase. This enzyme acts reversely to the action of thrombin, that is, it acts to dissolve fibrin. For this reason, plasmin plays an important role in securing blood flow through capillaries. However, when this enzyme becomes abnormally activated for some reason, it causes hemorrhagic diseases. This enzyme participates also in inflammation, increasing the vascular permeability and causing edema or the like. Therefore, an inhibitor for this enzyme is useful as a drug to treat hemorrhagic diseases and inflammation.

III. Kallikrein

Kallikrein is an enzyme widely distributed in blood and other organs and glands, usually in the form of its precursor prekallikrein which is activated with Hageman factor or other proteases. This enzyme participates in the hypotensive kallikrein-kinin system which counteracts the hyper tensive reninangiotensin system and plays an important role in the control of blood pressure. This enzyme particpates also in exogenous coagulation system. Further, kallikrein originated from organs or glands plays an important role in the improvement of local circulation. However, an abnormal activation, particularly an abnormal local activation, of this enzyme causes an insufficiency of local circulation due to the exaggeration of coagulation system, causing inflammation, ulcer, or the like. Therefore, a kallikrein inhibitor is useful for the control of blood pressure and as a drug for the treatment of inflammation or ulcer.

IV. Thrombin

Thrombin is known as an enzyme having a blood coagulating activity. In normal state, thrombin is formed by the activation of prothrombin in the blood when the vascular wall is injured. Thrombin acts to decompose the fibrinogen in the blood into fibrin. The resulting fibrin deposits on the injured part of vascular wall to prevent plasma components from transudation and simultaneously to promote the restoration of tissues. However, when the coagulation system is abnormally activated for some reason, a large number of fine thrombus are formed in capillaries throughout the entire body. Therefore, the present compound is useful as a drug for the treatment of such a disease.

The present compound and its pharmaceutically acceptable acid addition salts possess a strong C1 esterase ($C\bar{1}r$, $C\bar{1}s$) inhibitory activity, an ability of inhibiting the complement mediated hemolysis, and a therapeutic activity against the Masugi Nephritis in which the activation of the complement system caused by an immune complex is said to play an important role. This indicates that the present compound is useful as an anti-complement agent effective for the treatment of allergic diseases such as nephritis associated with the complement.

The role of complement in the living body, the interrelation between a disease and the complement, the clinical significance of inhibitor, and the significance of tests (inhibition of $C\bar{1}r$, $C\bar{1}s$, complement mediated hemolysis, and Masugi nephritis) performed by the present inventors are described below.

Anti-complement activity (1) $C\bar{1}r$, $C\bar{1}s$

The complement is one of the serum components and comprises 9 components of C1 to C9. C1 is separated into 3 subcomponents of C1q, $C\bar{1}r$ and $C\bar{1}s$. $C\bar{1}s$ and $C\bar{1}r$ means activated C1s and activated C1r, respectively. The complenent was thought at first to perform a part of the infection protective process of living body, since it shows bacteriolysis, but recently an intimate relation to the immunity has been evident. It was shown that the complement is activated by the immune complex progressively from C1 to C9 and exhibits cytolysis or hemolysis at the final stage (activation of C9). It was also disclosed that the fragments (e.g. C3a, C5a) liberated in the course of activation of the complement system exaggerate the vascular permeability and promote the chemotaxis of polymorphonuclear leucocytes or immune adherence. Since that time, the interrelationship between the abnormal activation of complement and various diseases, particularly immune diseases, has been extensively investigated and, as the result, the intimate association of autoimmune diseases with the complement is beginning to be disclosed. Examples of autoimmune diseases caused by the abnormal activation of complement include autoimmune hemolytic anemia, autoimmune thrombocytophenia, leukopenia, glomerulonephritis, systemic lupus erythematosus, serum sickness and periarteritis nodosa. It is expectable to cure such diseases by inhibiting the activation of complement or inhibiting the activated complement in an early stage. The present inventors examined the C1 esterase inhibitory effect of the present compound by using C1 esterase as target enzyme and, in addition, the influence of the present compound on the complement system to estimate the usefulness of the present compound as a drug for the treatment of autoimmune diseases.

(2) Complement mediated hemolysis

The complement mediated hemolysis is widely used as a means to determine the titration of complement. The principle of this method is based on the fact that hemolysis if caused by the activation of complement, when the latter is added to a complex (immune complex) of erythrocytes and the antibody thereof. The degree of hemolysis varies in proportion to the amount of complement added. Therefore, when a known amount of complement admixed with a C1 esterase inhibitor is used, the hemolysis must be suppressed in proportion to the inhibitory activity. The present compound having C1 esterase inhibitory activity showed strong inhibition of complement mediated hemolysis as shown hereinafter.

(3) Masugi's nephritis

Masugi nephritis is known to be an experimental nephritic model closely resembling the human glomerulonephritis. This nephritic model may be induced in rats by injection of heterologus anti-rat-kidney serum. For the onset of Masugi's nephritis, an important role is played by the activation of complement system induced by the antigen-antibody reaction. It is, therefore, expectable that a compound having a C1-esterase inhibitory activity will improve the progress of Masugi nephritis.

The protein content of the animal's urine is used as the parameter for the progress of Masugi nephritis. As shown in Table 3, Compound No. 69 of the present invention distinctly decreased the protein content of urine. From the result, it may be said that the compound of this invention having a Cl-esterase inhibitory activity is useful as a remedy for the glomerulonephritis and is also useful as a remedy for autoimmune diseases inclusive of glomerulonephritis.

[Anti-trypsin, anti-plasmin, anti-kallikrein and anti-thrombin activities]

The anti-trypsin, anti-plasmin, anti-kallikrein and anti-thrombin activities were determined according to the method of Muramatsu et al. [M. Muramatsu, T. Onishi, S. Makino, Y. Hayashi and S. Fujii, J. of Biochem., 58, 214 (1965)]. The results were as shown in Table 1. The data summarized in Table 1 are expressed in terms of molar concentration ($ID_{50}$) of the test compound which inhibits 50% of the activity of each enzyme to hydrolyze TAME (tosylarginine methyl ester). The compound No. corresponds to the compound number shown in Examples.

TABLE 1

| Compound No. | Trypsin | Plasmin | Kallikrein | Thrombin |
|---|---|---|---|---|
| 1 | $>10^{-5}$ | $>10^{-5}$ | $>10^{-5}$ | $>10^{-5}$ |
| 2 | $>10^{-5}$ | $>10^{-5}$ | $>10^{-5}$ | $>10^{-5}$ |
| 3 | | | | |
| 4 | | | | |
| 5 | $7 \times 10^{-7}$ | $3 \times 10^{-7}$ | $1 \times 10^{-6}$ | $2 \times 10^{-6}$ |
| 6 | $2 \times 10^{-7}$ | $4 \times 10^{-7}$ | $3 \times 10^{-7}$ | $8 \times 10^{-8}$ |
| 7 | $>10^{-5}$ | $4 \times 10^{-6}$ | $>10^{-5}$ | $5 \times 10^{-7}$ |
| 8 | $2 \times 10^{-6}$ | $2 \times 10^{-6}$ | $3 \times 10^{-6}$ | $1 \times 10^{-7}$ |
| 9 | | | | |
| 10 | $>10^{-5}$ | $>10^{-5}$ | $>10^{-5}$ | $2 \times 10^{-6}$ |
| 11 | $>10^{-5}$ | $>10^{-5}$ | $>10^{-5}$ | $>10^{-5}$ |
| 12 | $6 \times 10^{-6}$ | $>10^{-5}$ | $>10^{-5}$ | $4 \times 10^{-6}$ |
| 13 | $>10^{-5}$ | $>10^{-5}$ | $>10^{-5}$ | $>10^{-5}$ |
| 14 | $10^{-5}$ | $10^{-5}$ | $10^{-5}$ | $10^{-5}$ |
| 15 | | | | |
| 16 | $1 \times 10^{-5}$ | $3 \times 10^{-7}$ | $5 \times 10^{-6}$ | $1 \times 10^{-6}$ |
| 17 | $>10^{-5}$ | $>10^{-5}$ | $>10^{-5}$ | $>10^{-5}$ |
| 18 | $3 \times 10^{-7}$ | $5 \times 10^{-7}$ | $1 \times 10^{-6}$ | $4 \times 10^{-6}$ |
| 19 | $>10^{-5}$ | $>10^{-5}$ | $>10^{-5}$ | $>10^{-5}$ |
| 20 | $1 \times 10^{-6}$ | $6 \times 10^{-7}$ | $6 \times 10^{-7}$ | $5 \times 10^{-7}$ |
| 21 | $>10^{-5}$ | $>10^{-5}$ | $>10^{-5}$ | $>10^{-5}$ |
| 22 | $>10^{-5}$ | $>10^{-5}$ | $>10^{-5}$ | $2 \times 10^{-6}$ |
| 23 | $1 \times 10^{-5}$ | $2 \times 10^{-5}$ | $6 \times 10^{-5}$ | $2 \times 10^{-7}$ |
| 24 | $3 \times 10^{-6}$ | $>10^{-5}$ | $>10^{-5}$ | $4 \times 10^{-6}$ |
| 25 | $3 \times 10^{-7}$ | $6 \times 10^{-7}$ | $>10^{-5}$ | $1 \times 10^{-7}$ |
| 26 | $4 \times 10^{-7}$ | $4 \times 10^{-7}$ | $2 \times 10^{-6}$ | $6 \times 10^{-8}$ |
| 27 | $3 \times 10^{-7}$ | $4 \times 10^{-7}$ | $4 \times 10^{-6}$ | $1 \times 10^{-7}$ |
| 28 | $1 \times 10^{-5}$ | $7 \times 10^{-6}$ | $>10^{-5}$ | $3 \times 10^{-6}$ |
| 29 | $8 \times 10^{-7}$ | $4 \times 10^{-7}$ | $1 \times 10^{-6}$ | $3 \times 10^{-8}$ |
| 30 | $3 \times 10^{-7}$ | $4 \times 10^{-7}$ | $2 \times 10^{-7}$ | $3 \times 10^{-8}$ |
| 31 | $8 \times 10^{-6}$ | $3 \times 10^{-6}$ | $4 \times 10^{-5}$ | $2 \times 10^{-5}$ |
| 32 | | | | |
| 33 | $>10^{-5}$ | $>10^{-5}$ | $>10^{-5}$ | $>10^{-5}$ |
| 34 | $4 \times 10^{-6}$ | $4 \times 10^{-6}$ | $>10^{-5}$ | $3 \times 10^{-6}$ |
| 35 | $1 \times 10^{-6}$ | $5 \times 10^{-6}$ | $>10^{-5}$ | $3 \times 10^{-6}$ |
| 36 | | | | |
| 37 | $5 \times 10^{-8}$ | $4 \times 10^{-7}$ | $7 \times 10^{-7}$ | $3 \times 10^{-7}$ |
| 38 | $2 \times 10^{-8}$ | $4 \times 10^{-7}$ | $1 \times 10^{-6}$ | $2 \times 10^{-7}$ |

TABLE 1-continued

| Compound No. | Trypsin | Plasmin | Kallikrein | Thrombin |
|---|---|---|---|---|
| 39 | $1 \times 10^{-8}$ | $2 \times 10^{-7}$ | $4 \times 10^{-7}$ | $2 \times 10^{-7}$ |
| 40 | | | | |
| 41 | | | | |
| 42 | $7 \times 10^{-8}$ | $3 \times 10^{-7}$ | $3 \times 10^{-7}$ | $7 \times 10^{-8}$ |
| 43 | | | | |
| 44 | $2 \times 10^{-8}$ | $3 \times 10^{-6}$ | $3 \times 10^{-7}$ | $2 \times 10^{-6}$ |
| 45 | $2 \times 10^{-8}$ | $3 \times 10^{-7}$ | $4 \times 10^{-7}$ | $2 \times 10^{-7}$ |
| 46 | $5 \times 10^{-8}$ | $6 \times 10^{-7}$ | $3 \times 10^{-7}$ | $4 \times 10^{-8}$ |
| 47 | $>10^{-5}$ | $>10^{-5}$ | $>10^{-5}$ | $>10^{-5}$ |
| 48 | $2 \times 10^{-6}$ | $2 \times 10^{-7}$ | $8 \times 10^{-6}$ | $4 \times 10^{-7}$ |
| 49 | $3 \times 10^{-8}$ | $2 \times 10^{-7}$ | $4 \times 10^{-7}$ | $<10^{-8}$ |
| 50 | $4 \times 10^{-6}$ | $5 \times 10^{-7}$ | $>10^{-5}$ | $2 \times 10^{-7}$ |
| 51 | $2 \times 10^{-7}$ | $3 \times 10^{-7}$ | $>10^{-5}$ | $9 \times 10^{-7}$ |
| 52 | $3 \times 10^{-6}$ | $2 \times 10^{-7}$ | $>10^{-5}$ | $9 \times 10^{-8}$ |
| 53 | | | | |
| 54 | $2 \times 10^{-8}$ | $3 \times 10^{-7}$ | $4 \times 10^{-7}$ | $9 \times 10^{-8}$ |
| 55 | | | | |
| 56 | $5 \times 10^{-8}$ | $3 \times 10^{-7}$ | $4 \times 10^{-7}$ | $6 \times 10^{-8}$ |
| 57 | $2 \times 10^{-6}$ | $2 \times 10^{-7}$ | $3 \times 10^{-6}$ | $8 \times 10^{-6}$ |
| 58 | $8 \times 10^{-6}$ | $8 \times 10^{-6}$ | $2 \times 10^{-6}$ | $>10^{-5}$ |
| 59 | $5 \times 10^{-7}$ | $7 \times 10^{-8}$ | $7 \times 10^{-7}$ | $4 \times 10^{-6}$ |
| 60 | $1 \times 10^{-6}$ | $4 \times 10^{-6}$ | $2 \times 10^{-6}$ | $>10^{-5}$ |
| 61 | $2 \times 10^{-7}$ | $2 \times 10^{-7}$ | $1 \times 10^{-6}$ | $4 \times 10^{-7}$ |
| 62 | $5 \times 10^{-7}$ | $3 \times 10^{-6}$ | $2 \times 10^{-6}$ | $5 \times 10^{-4}$ |
| 63 | | | | |
| 64 | | | | |
| 65 | | | | |
| 66 | $1 \times 10^{-8}$ | $4 \times 10^{-7}$ | $2 \times 10^{-7}$ | $2 \times 10^{-7}$ |
| 67 | | | | |
| 68 | | | | |
| 69 | $8 \times 10^{-8}$ | $2 \times 10^{-6}$ | $4 \times 10^{-7}$ | $2 \times 10^{-7}$ |
| 70 | $3 \times 10^{-8}$ | $7 \times 10^{-7}$ | $4 \times 10^{-5}$ | $5 \times 10^{-7}$ |
| 71 | $4 \times 10^{-8}$ | $2 \times 10^{-6}$ | $3 \times 10^{-5}$ | $2 \times 10^{-6}$ |

[Anti-complement activity]

(1) Anti-Cl ($\overline{Clr}$, $\overline{Cls}$) activity and inhibition of complement mediated hemolysis:

The anti-Cl esterase ($\overline{Clr}$, $\overline{Cls}$) activity was determined according to the method of Okamura et al. [K. Okamura, M. Muramatsu and B. Fujii, Biochem. Biophys. Acta, 295, 252–257 (1973)]. The inhibition of complement mediated hemolysis was determined according to the method of Baker et al. [B. R. Baker and E. H. Erickson, J. Med. Chem., 12, 408–414 (1969)]. The results obtained were as shown in Table 2. The figures in Table 2 have the following meanings:

$\overline{Clr}$: Molar concentration of the test compound which inhibits 50% of the ability of $\overline{Clr}$ to hydrolyse AAME (acetylarginin methyl ester) ($ID_{50}$).

$\overline{Cls}$: Molar concentration of the test compound which inhibits 50% of the ability of $\overline{Cls}$ to hydrolyse ATEE (acetyltyrosin ethyl ester).

Inhibition of complement mediated hemolysis (%): The inhibitory activity is shown in terms of percent inhibition of the compound at varied concentrations.

Compound No.: The compound number shown in Examples.

TABLE 2

| Compound No. | Anti-Cl activity $\overline{Clr}$ | Anti-Cl activity $\overline{Cls}$ | Inhibition of complement mediated hemolysis (%) $1 \times 10^{-4}$ | $1 \times 10^{-5}$ | $1 \times 10^{-6}$ | $1 \times 10^{-7}$ |
|---|---|---|---|---|---|---|
| 1 | $>10^{-5}$ | | 95.9 | 37.3 | 16.0 | 0 |
| 2 | NE | | 97.3 | 30.1 | 3.9 | 2.1 |
| 3 | | | 44.4 | 5.0 | 18.0 | 0 |
| 4 | | | 95.0 | 67.2 | 8.7 | 0 |
| 5 | $5 \times 10^{-6}$ | $9 \times 10^{-7}$ | 100 | 97.0 | 47.2 | 3.0 |
| 6 | $1 \times 10^{-6}$ | $3 \times 10^{-7}$ | 100 | 97.7 | 52.9 | 5.0 |
| 7 | $>10^{-5}$ | | 99.0 | 78.2 | 10.2 | 1.7 |
| 8 | $>10^{-5}$ | | 199.0 | 90.5 | 22.0 | 0 |
| 9 | | | 171.6 | 16.2 | 2.5 | 0 |
| 10 | $>10^{-5}$ | | 95.9 | 80.3 | 17.0 | 2.3 |

TABLE 2-continued

| Compound No. | Anti-C1 activity | | Inhibition of complement mediated hemolysis (%) | | | |
|---|---|---|---|---|---|---|
| | $\overline{C1r}$ | $\overline{C1s}$ | $1 \times 10^{-4}$ | $1 \times 10^{-5}$ | $1 \times 10^{-6}$ | $1 \times 10^{-7}$ |
| 11 | $>10^{-5}$ | | 17.4 | 2.5 | 2.5 | 3.5 |
| 12 | $>10^{-5}$ | $5 \times 10^{-6}$ | 91.3 | 57.8 | 15.0 | 3.8 |
| 13 | $>10^{-5}$ | $>10^{-5}$ | 15.9 | 9.8 | 0 | 0 |
| 14 | $>10^{-5}$ | $>10^{-5}$ | 63.6 | 16.2 | 7.0 | 0 |
| 15 | | | 98.8 | 81.7 | 12.7 | 0 |
| 16 | $>10^{-5}$ | $8 \times 10^{-7}$ | 91.2 | 61.8 | 17.4 | 3.4 |
| 17 | $>10^{-5}$ | $>10^{-5}$ | 98.6 | 78.2 | 20.4 | 0 |
| 18 | $>10^{-5}$ | $2 \times 10^{-6}$ | 98.8 | 73.2 | 11.4 | 2.2 |
| 19 | $>10^{-5}$ | $>10^{-5}$ | 99.2 | 83.4 | 15.0 | 5.0 |
| 20 | $>10^{-5}$ | $3 \times 10^{-7}$ | 96.8 | 80.3 | 13.0 | 1.8 |
| 21 | $>10^{-5}$ | $4 \times 10^{-6}$ | 99.3 | 99.9 | 60.2 | 10.9 |
| 22 | $6 \times 10^{-6}$ | $>10^{-5}$ | 22.8 | 0 | 0 | 0 |
| 23 | $7 \times 10^{-6}$ | $5 \times 10^{-6}$ | | | | |
| 24 | $>10^{-5}$ | $2 \times 10^{-6}$ | 88.2 | 29.1 | 11.0 | 16.7 |
| 25 | $4 \times 10^{-6}$ | $2 \times 10^{-7}$ | 100.0 | 93.1 | 38.6 | 11.6 |
| 26 | $2 \times 10^{-7}$ | $3 \times 10^{-7}$ | 100.0 | 99.4 | 61.6 | 16.7 |
| 27 | $5 \times 10^{-7}$ | $2 \times 10^{-7}$ | 100 | 100 | 95.5 | 26.2 |
| 28 | $>10^{-5}$ | $3 \times 10^{-6}$ | 79.1 | 25.0 | 22.8 | 23.8 |
| 29 | $3 \times 10^{-6}$ | $3 \times 10^{-7}$ | 98.4 | 97.9 | 67.8 | 8.0 |
| 30 | $9 \times 10^{-7}$ | $3 \times 10^{-7}$ | 100 | 100 | 99.0 | 45.3 |
| 31 | $2 \times 10^{-6}$ | $3 \times 10^{-6}$ | 97.2 | 80.5 | 15.8 | 1.8 |
| 32 | | | 63.9 | 97.5 | 7.1 | 0 |
| 33 | $>10^{-5}$ | $>10^{-5}$ | 94.1 | 20.4 | 0 | 0 |
| 34 | $3 \times 10^{-6}$ | $3 \times 10^{-6}$ | 99.6 | 96.7 | 53.7 | 12.4 |
| 35 | $4 \times 10^{-7}$ | $3 \times 10^{-7}$ | 88.8 | 43.9 | 29.9 | 11.8 |
| 36 | | | 100 | 100 | 100 | 90.4 |
| 37 | $4 \times 10^{-8}$ | $6 \times 10^{-8}$ | 95.9 | 37.3 | 16.0 | 0 |
| 38 | $3 \times 10^{-7}$ | $3 \times 10^{-7}$ | 98.6 | 100 | 96.1 | 37.2 |
| 39 | $4 \times 10^{-7}$ | $2 \times 10^{-7}$ | 0 | 95.4 | 96.8 | 52.1 |
| 40 | | | 87.5 | 68.1 | 7.8 | 2.0 |
| 41 | | | 66.7 | 9.3 | 0 | 0 |
| 42 | $1 \times 10^{-6}$ | $4 \times 10^{-8}$ | 100 | 99.1 | 70.0 | 7.6 |
| 43 | | | 95.0 | 50.4 | 3.7 | 0 |
| 44 | $4 \times 10^{-6}$ | $6 \times 10^{-7}$ | 99.1 | 94.1 | 29.0 | 29.2 |
| 45 | $9 \times 10^{-7}$ | $4 \times 10^{-7}$ | 0 | 90.2 | 6.0 | 0 |
| 46 | $2 \times 10^{-6}$ | $9 \times 10^{-8}$ | 100 | 98.0 | 67.6 | 5.0 |
| 47 | $>10^{-5}$ | $3 \times 10^{-8}$ | 33.5 | 10.4 | 13.4 | 0 |
| 48 | $>10^{-5}$ | $3 \times 10^{-6}$ | 94.0 | 94.8 | 75.3 | 23.2 |
| 49 | $1 \times 10^{-6}$ | | 83.8 | 94.6 | 97.5 | 75.1 |
| 50 | $9 \times 10^{-6}$ | $>10^{-5}$ | 98.8 | 75.4 | 6.9 | 0 |
| 51 | $>10^{-5}$ | $3 \times 10^{-6}$ | 99.1 | 90.9 | 15.0 | 0 |
| 52 | $5 \times 10^{-6}$ | $3 \times 10^{-6}$ | 100 | 98.8 | 75.4 | 12.8 |
| 53 | | | 87.5 | 25.2 | — | 3.5 |
| 54 | $2 \times 10^{-6}$ | $2 \times 10^{-7}$ | 99.1 | 98.6 | 79.4 | 41.1 |
| 55 | | | 100 | 96.9 | 60.8 | 3.5 |
| 56 | $1 \times 10^{-6}$ | $5 \times 10^{-7}$ | 99.1 | 98.1 | 88.1 | 20.4 |
| 57 | $>10^{-5}$ | $2 \times 10^{-6}$ | 70.5 | 14.8 | 2.3 | 0 |
| 58 | $>10^{-5}$ | $4 \times 10^{-6}$ | 93.4 | 20.0 | 3.0 | 0 |
| 59 | $2 \times 10^{-6}$ | $3 \times 10^{-7}$ | 100 | 100 | 76.0 | 15.6 |
| 60 | $3 \times 10^{-6}$ | $8 \times 10^{-7}$ | 100 | 100 | 89.8 | 44.4 |
| 61 | $4 \times 10^{-7}$ | $3 \times 10^{-7}$ | 98.6 | 100 | 98.0 | 76.1 |
| 62 | $5 \times 10^{-7}$ | $6 \times 10^{-7}$ | 100 | 100 | 100 | 95.4 |
| 63 | | | 100 | 100 | 98.0 | 94.5 |
| 64 | | | 100 | 100 | 97.1 | 75.7 |
| 65 | | | 81.7 | 9.8 | 0 | 0 |
| 66 | $3 \times 10^{-6}$ | $4 \times 10^{-8}$ | 99.1 | 96.4 | 41.7 | 0 |
| 67 | | | 99.2 | 99.2 | 96.9 | 57.5 |
| 68 | | | 100 | 92.9 | 50.6 | 5.8 |
| 69 | $2 \times 10^{-6}$ | $4 \times 10^{-7}$ | 100 | 99.6 | 86.5 | 7.2 |
| 70 | $3 \times 10^{-6}$ | $2 \times 10^{-7}$ | 100 | 100 | 97.0 | 46.1 |
| 71 | $4 \times 10^{-6}$ | $7 \times 10^{-7}$ | 90.6 | 35.3 | 2.7 | 9.0 |
| 72 | $1 \times 10^{-6}$ | $2 \times 10^{-7}$ | 100 | 87.8 | 10.8 | 0 |
| 73 | | | 100 | 100 | 89.9 | 46.1 |
| 74 | $>10^{-5}$ | $3 \times 10^{-6}$ | 55.4 | 5.7 | 3.6 | 0 |
| 75 | $8 \times 10^{-6}$ | $3 \times 10^{-6}$ | 45.2 | 3.2 | 0 | 0 |
| 76 | $>10^{-5}$ | $>10^{-5}$ | 34.8 | 4.8 | 0 | 0 |
| 77 | $>10^{-5}$ | $8 \times 10^{-7}$ | 97.3 | 48.9 | 1.8 | 0 |
| 78 | $>10^{-5}$ | | 97.4 | 58.8 | 7.0 | 0 |
| 79 | $>10^{-5}$ | | 95.1 | 96.8 | 81.7 | 48.1 |
| 80 | $>10^{-5}$ | $>10^{-5}$ | 66.5 | 6.9 | 0 | 0 |
| 81 | $>10^{-5}$ | $>10^{-5}$ | 98.2 | 71.6 | 4.2 | 0 |
| 82 | $>10^{-5}$ | $>10^{-5}$ | 29.8 | 0 | 0 | 0 |
| 83 | $9 \times 10^{-6}$ | $4 \times 10^{-6}$ | 100 | 90.2 | 12.9 | — |
| 84 | $>10^{-5}$ | $4 \times 10^{-7}$ | 98.6 | 67.7 | 2.0 | 0 |
| 85 | $6 \times 10^{-7}$ | $5 \times 10^{-7}$ | 98.6 | 97.9 | 67.1 | 7.0 |
| 86 | | | 100 | 97.1 | 53.6 | 11.0 |
| 87 | $>10^{-5}$ | $5 \times 10^{-6}$ | 0 | 0 | 0 | 0 |

TABLE 2-continued

| Compound No. | Anti-C1 activity | | Inhibition of complement mediated hemolysis (%) | | | |
|---|---|---|---|---|---|---|
| | C1r̄ | C1s̄ | $1 \times 10^{-4}$ | $1 \times 10^{-5}$ | $1 \times 10^{-6}$ | $1 \times 10^{-7}$ |
| Leupeptin | $2 \times 10^{-4}$ | $2 \times 10^{-5}$ | 97 | 52 | 0 | 0 |

(3) Masugi nephritis.

Pharmacological test (Therapeutic experiment on Masugi's nephritis).

Experimental nephritis were induced in rats by intravenous injection of nephrotoxin prepared according to the method of Shibata et al. ["Experimental Immunoallergy.", p. 664 (1971), Bunkodo, Tokyo]. Each member of the medicine administered group had been orally administered with methanesulfonate of Compound No. 69 at a dose rate of 100 mg/kg body weight, twice a day, for eight consecutive days. On the second day from the beginning of medicine administration, nephrotoxin was intravenously administered. The effectiveness was evaluated by determining the difference in protein content of urine between the nephritic group (control group) and the medicine administered group on the 6th day (5th day after the administration of nephrotoxin) and 9th day from the beginning of medicine administration. The results obtained were as shown in Table 3.

TABLE 3

|  | 5th day | 8th day |
|---|---|---|
| Percentage inhibition | 81% | 39% |

The percentage inhibition indicates the degree of decrease in protein content of urine of the medicine administered group as compared with the control group. Method of administration:

The present compound is most suitably administered orally, though can be administered by injection. It is used as a drug either alone or in combination with other drugs. It is administered generally in the form of medicinal composition, though can be administered as simple substance without any additive. Examples of medicinal compositions include tablets, powderes, capsules, syrups and solutions. An oral composition may contain common additives such as binders, diluents, lubricants, disintegrators and excipients. Oral solutions may be in the form of aqueous or oily suspension, solution, emulsion, syrup or elixir, or in the form of dry syrup which, before use, is readjusted with water or other suitable solvents. The solutions may contain common additives such as suspending agents, flavoring agents, diluents, or emulsifies. For injection, may be used aqueous suspensions or oily suspensions.

Dosage

The present compound may be administered to mammals (including man) orally at a dose of 10 to 200 mg per day or by intravenous injection at a dose of 1 to 20 mg per day. However, these doses are presented solely for the sake of example. A suitable dose for a patient should be determined depending upon the age and body weight of the patient and the features of illness.

Examples of pharmaceutical formulations are described below.

Examples of pharmaceutical formulations:

(1) Capsules.

| The present compound | 100.0 mg |
|---|---|
| Lactose | 59.0 |
| Crystalline cellulose | 33.4 |
| Calcium carboxymethylcellulose | 3.6 |
| Magnesium stearate | 4.0 |
| Total | 200.0 mg |

(2) Fine granules.

| The present compound | 50.0 mg |
|---|---|
| Lactose | 249.0 |
| Mannitol | 75.0 |
| Corn starch | 110.0 |
| Hydroxypropylcellulose | 16.0 |
| Total | 500.0 mg |

(3) Injections.

| The present compound | 5.0 mg |
|---|---|
| Water for injection | 2 ml |

Made up to injections in a customary manner.

Toxicity

The median lethal dose ($LD_{50}$) of the present compound is as shown in Table 4.

TABLE 4

| Compound No. | $LD_{50}$ mg/kg | |
|---|---|---|
| | IP | PO |
| 69 | 192 | 1,700 |
| 70 | 200 | 2,500 |

Examples of preparation of the present compounds are described below. The physical data of each compound are summarized in Table 5.

EXAMPLE 1

Synthesis of 4-amidino-2-benzoylphenyl acetate

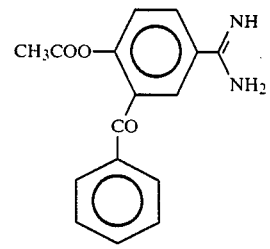

Compound No. 1

Into 30 ml of dried pyridine, was dissolved 5.0 g of 4-amidino-2-benzoylphenol methanesulfonate. To the solution, while being cooled in ice and stirred, was added slowly a solution of 1.2 g of acetyl chloride in 5 ml of dried DMF. After stirring at room temperature for one hour, the mixture was filtered to remove a precipitate and the precipitate was washed with pyridine. Upon addition of ethyl ether an oily matter separated out of the filtrate. The oily matter was washed a few times with ethyl ether and dissolved in water. A saturated aqueous sodium hydrogen-carbonate solution was added to the resulting aqueous solution to precipitate the carbonate of Compound No. 1. The carbonate which was collected by filtration was washed with water, then with acetone and dried to obtain 3.5 g of the anhydrous carbonate. The anhydrous carbonate was suspended in 10 ml of methanol and admixed with 1.2 g of methanesulfonic acid. The crystals disappeared by dissolution, but after a while colorless crystal precipitated again. After addition of ethyl ether, the crystals were collected by filtration, and recrystallized from ethanol to obtain 2.5 g of colorless needle crystals of 4-amidino-2-benzoylphenyl acetate methanesulfonate.

EXAMPLE 2

Synthesis of 4-amidino-2-nitrophenyl acetate

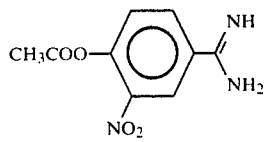

Compound No. 2

To a suspension of 3.0 g of 4-amidino-2-nitrophenol methanesulfonate in 15 ml of acetic anhydride, was added 0.5 ml of methanesulfonic acid. The mixture was refluxed with stirring for 10 to 20 minutes. The crystals dissolved slowly, forming a clear yellow solution. Upon standing at room temperature, colorless crystals separated out of the solution. The crystals were ashed with ethyl ether and recrystallized from ethanol to obtain 3.0 g of colorless needle crystals of 4-amidino-2-nitrophenyl acetate methanesulfonate.

EXAMPLE 3

Synthesis of 4-amidino-2-methoxyphenyl isovalerate

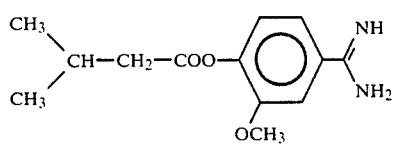

Compound No. 3

Into 40 ml of anhydrous pyridine, was dissolved 1.5 g of isovaleric acid. To the solution, while being cooled in ice, was added 3.7 g of DCC and the resulting mixture was stirred for 30 minutes. After addition of 3.9 g of 4-amidino-2-methoxyphenol methanesulfonate, the mixture was stirred overnight at room temperature. The precipitate which was formed was separated by filtration and washed with pyridine. Ethyl ether was added to the filtrate to precipitate colorless crystals. The crystals were washed with ethyl ether, dissolved in DMF, and recrystallized by adding ethyl ether. The crystals were further purified by recrystallizing from an ethanol-ethyl ether mixture to obtain 3.4 g of colorless flaky crystals of 4-amidino-2-methoxyphenyl isovalerate methanesulfonate.

EXAMPLE 4

The procedures similar to those of Examples 1 to 3 were followed to obtain the following compounds:

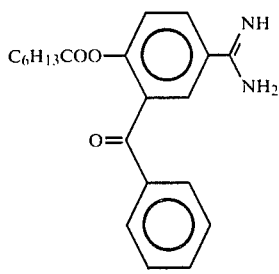

Compound No. 4

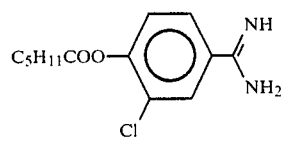

Compound No. 5

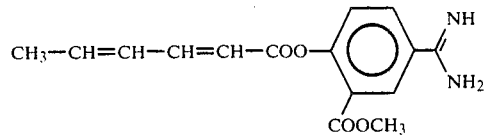

Compound No. 6

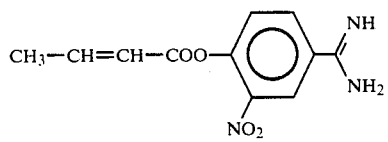

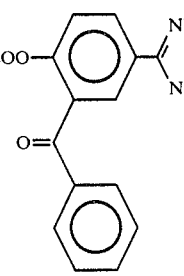

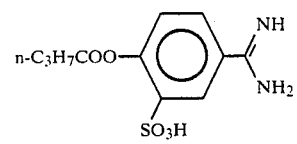

EXAMPLE 5

Synthesis of 4-amidino-2-nitrophenyl cyclopropanecarboxylate

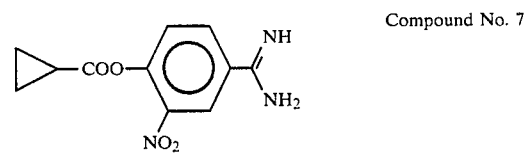

Compound No. 7

In 5.0 ml of cyclopropanecarboxyl chloride, was suspended 2.0 g of 4-amidino-2-nitrophenol methanesulfonate. After addition of 2 drops of methanesulfonic acid, the suspension was heated with vigorous stirring in an oil bath at 80° C. The temperature of the oil bath was gradually elevated to keep the suspension refluxing, whereby the crystals gradually dissolved. The refluxing was continued for a while when suddenly the whole mixture turned into a pale yellow solid mass. The solid mass was washed out of the vessel with ethyl ether and recrystallized from ethanol to obtain 2.0 g of pale yellow granular crystals of 4-amidino-2-nitrophenyl cyclopropanecarboxylate methanesulfonate.

EXAMPLE 6

The following compounds were obtained in a manner similar to that in Example 1, 2, 3 or 5:

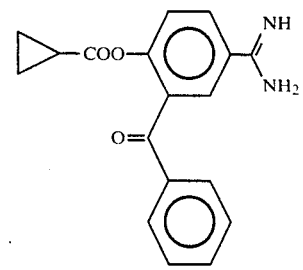

Compound No. 8

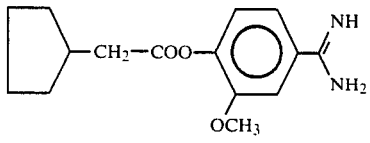

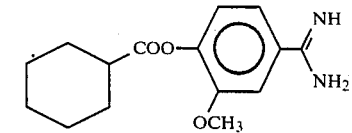

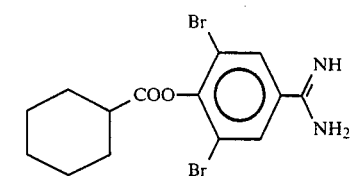

Compound No. 9

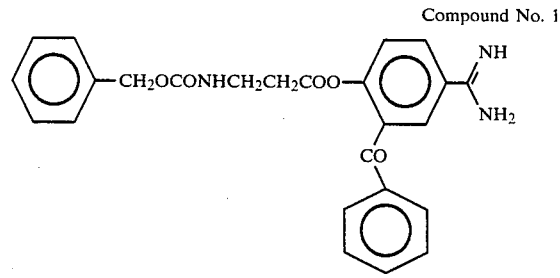

EXAMPLE 7

Synthesis of 4-amidino-2-benzoylphenyl 3-benzyloxycarbonylaminopropionate

Compound No. 10

Into 50 ml of anhydrous pyridine, was dissolved 3.3 g of 3-benzyloxycarbonylaminopropionic acid. To the solution, while being cooled in ice, was added 3.7 g of DCC. The mixture was stirred for 30 minutes. After addition of 5.0 g of 4-amidino-2-benzoylphenol methanesulfonate, the mixture was further stirred overnight. The precipitate which was formed was separated by filtration and washed with pyridine. Ethyl ether was added to the filtrate to separate an oily substance which solidified upon stirring. The solidified substance was collected by filtration, washed with ethyl ether, and dissolved in DMF. The crystals precipitated out of the DMF solution by the addition of ethyl ether were recrystallized from ethanol to yield 3.9 g of colorless granular crystals of 4-amidino-2-benzoylphenyl 3-benzyloxycarbonylaminopropionate methanesulfonate.

EXAMPLE 8

Synthesis of 4-amidino-2-benzoylphenyl 3-aminopropionate

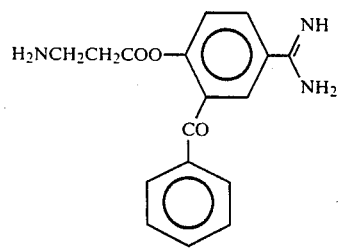

Compound No. 11

To 4.0 ml of a 30% hydrogen bromide-acetic acid mixture, was added 1.0 g of 4-amidino-2-benzoylphenyl 3-benzyloxycarbonylaminopropionate methanesulfonate. The mixture was stirred for one hour at room temperature to dissolve the crystals, forming a homogeneous yellow solution. Anhydrous ethyl ether was added to the solution to precipitate a white or pale yellow powder. After removing the supernatant, the residue was washed a few times with ethyl ether to obtain 0.5 g of a hygroscopic powder of 4-amidino-2-benzoylphenyl 3-aminopropionate dihydrobromide.

EXAMPLE 9

Synthesis of 4-amidino-2-benzoylphenyl 6-benzyloxycarbonylaminocaproate

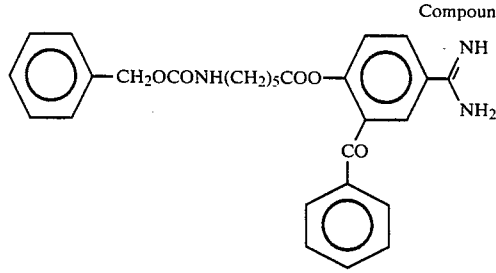

Compound No. 12

Into 50 ml of anhydrous pyridine, was dissolved 4.0 g of 6-benzyloxycarbonylaminocaproic acid. To the solution, while being cooled in ice, was added 3.7 g of DCC. After having been stirred for 30 minutes, the mixture was admixed with 5.0 g of 4-amidino-2-benzoylphenol methanesulfonate and stirred overnight at room temperature. The precipitate which was formed was separated by filtration and washed with pyridine. Ethyl ether was added to the filtrate to precipitate white crystals. The crystals were collected by filtration, washed with ethyl ether, dissolved in DMF, and admixed with ethyl ether to precipitate colorless crystals which were collected by filtration and dried to obtain 5.7 g of an anhydrous substance. This substance was recrystallized from ethanol to obtain 2.7 g of colorless needle crystals of 4-amidino 2-benzoylphenyl 6-benzyloxycarbonylaminocaproate methanesulfonate.

EXAMPLE 10

Synthesis of 4-amidino-2-benzoylphenyl 6-aminocaproate

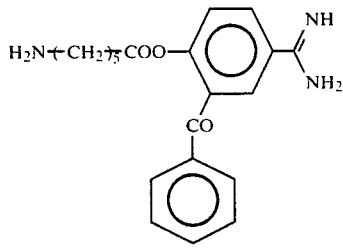

Compound No. 13

To 8.0 ml of a 30% hydrogen bromide-acetic acid mixture, was added 1.7 g of 4-amidino-2-benzoylphenyl 6-benzyloxycarbonylaminocaproate methanesulfonate. The mixture was stirred for one hour at room temperature, whereby the crystals dissolved in 4 to 5 minutes, forming a uniform solution. Upon addition of anhydrous ethyl ether to the solution, an oily substance separated out. The supernatant was removed and the oily substance was washed a few times with ethyl ether. The oily substance was dissolved with heating in a small volume of water, admixed with acetone, and stirred while cooling in ice, to obtain 0.9 g of a colorless powder of 4-amidino-2-benzoylphenyl 6-aminocaproate dihydrobromide.

EXAMPLE 11

Synthesis of 4-amidino-2-methoxyphenyl 6-guanidinocaproate

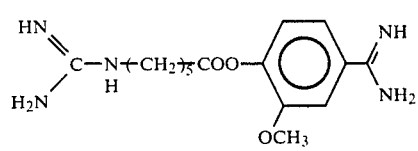

Compound No. 14

To 40 ml of anhydrous pyridine, was added 2.1 g of 6-guanidinocaproic acid hydrochloride. To the mixture, while being cooled in ice, was added 2.5 g of DCC. The mixture was stirred for one hour, admixed with 2.6 g of 4-amidino-2-methoxyphenol methanesulfonate, and further stirred overnight at room temperature. After addition of ethyl ether to the reaction mixture, the supernatant was removed to obtain an oily substance as the residue. The oily substance was dissolved in DMF, then freed from insolubles by filtration, and mixed with ethyl ether to obtain 4.0 g of a colorless oily substance. This substance was dissolved in water by heating, then treated with activated carbon, and mixed with acetone to isolate 3.5 g of 4-amidino-2-methoxyphenyl 6-guanidinocaproate methanesulfonate hydrochloride in the form of colorless oil.

EXAMPLE 12

Synthesis of 4-amidino-2-methoxycarbonylphenyl trans-4-benzyloxycarbonylaminomethylcyclohexanecarboxylate

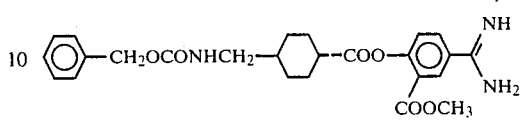

Compound No. 18

Into 40 ml of anhydrous pyridine, was dissolved 4.3 g of trans-4-benzyloxycarbonylaminomethylcyclohexanecarboxylic acid. To the solution, while being cooled in ice, was added 3.7 g of DCC. To the mixture which had been stirred for 30 minutes, was added 4.1 g of methyl 5-amidinosalicylate methanesulfonate. The mixture was stirred overnight at room temperature. The precipitate which was formed was separated by filtration and washed with pyridine. Ethyl ether was added to the filtrate and the precipitated white crystals were washed with ethyl ether and dissolved in DMF. The colorless crystals separated from the DMF solution by the addition of ethyl ether were recrystallized from ethanol to obtain 4.3 g of a colorless powder of 4-amidino-2-methoxycarbonylphenyl trans-4-benzyloxycarbonylamino-methylcyclohexanecarboxylate methanesulfonate.

EXAMPLE 13

Synthesis of 4-amidino-2-methyoxycarbonylphenyl trans-4-aminomethylcyclohexanecarboxylate

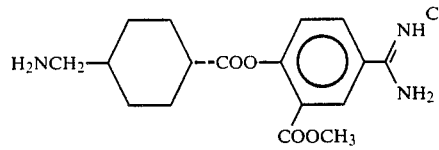

Compound No. 19

To 9.0 ml of a 30% hydrogen bromide-acetic acid mixture, was added 2.8 g of 4-amidino-2-methoxycarbonylphenyl trans-4-benzyloxycarbonylaminomethylcyclohexanecarboxylate methanesulfonate. The mixture was stirred for one hour at room temperature, meanwhile the crystals dissolved in a few minutes, forming a uniform yellow solution. The reaction mixture was mixed with ethyl ether, and the crystals were collected by filtration, washed with ethyl ether, and dried to obtain 3.1 g a dried product. The dried product was recrsytallized from ethanol to obtain 1.3 g of colorless granular crystals of 4-amidino-2-methoxycarbonylphenyl trans-4-aminomethylcyclohexane carboxylate dihydrobromide.

EXAMPLE 14

The following compounds were obtained by the procedures similar to those of Examples 7 to 13:

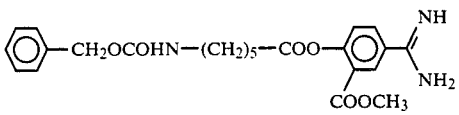

-continued

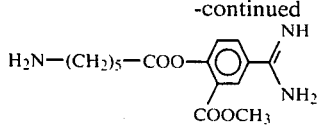

Compound No. 15

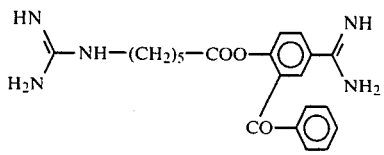

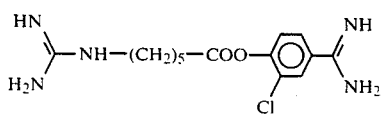

Compound No. 16

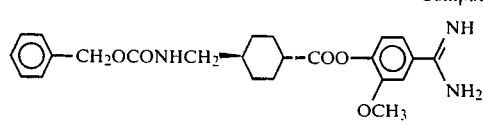

Compound 17

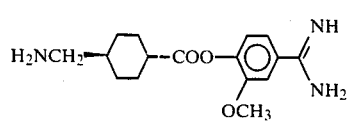

Compound No. 20

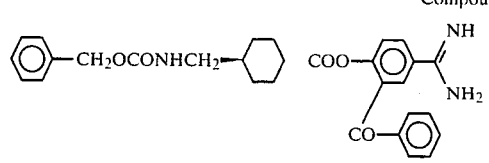

Compound No. 21

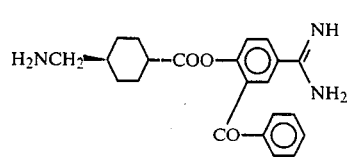

EXAMPLE 15a

Synthesis of 4-amidino-3-methylphenyl benzoate

Compound No. 22

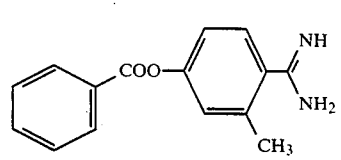

Into 4 ml of anhydrous pyridine, was dissolved 300 mg of 4-amidino-3-methylphenol methanesulfonate. To the solution, while being cooled in ice and stirred, was added slowly dropwise 171 mg of benzoyl chloride. The mixture was stirred for one hour at room temperature. The solid matter precipitated from the reaction mixture was separated by filtration and washed with a small volume of pyridine. The oily substance separated out of the filtrate by the addition of ethyl ether was dissolved in water and admixed with a saturated sodium hydrogen-carbonate solution to precipitate a white solid substance. This substance was collected by filtration and washed with water, then with ethyl ether to obtain 150 mg of the carbonate of captioned compound.

IR, $\nu_{max.}{}^{KBr}$, cm$^{-1}$: 3350, 2925, 2600, 1710, 1600, 1580.

The above carbonate was suspended in methanol and admixed with 60 mg of methanesulfonic acid. Upon addition of ethyl ether, there were obtained 160 mg of a white powder of 4-amidino-3-methylphenyl benzoate methanesulfonate.

EXAMPLE 15b

The 4-amidino-3-methylphenol methanesulfonate employed in Example 15-a had been synthesized according to the following reaction scheme:

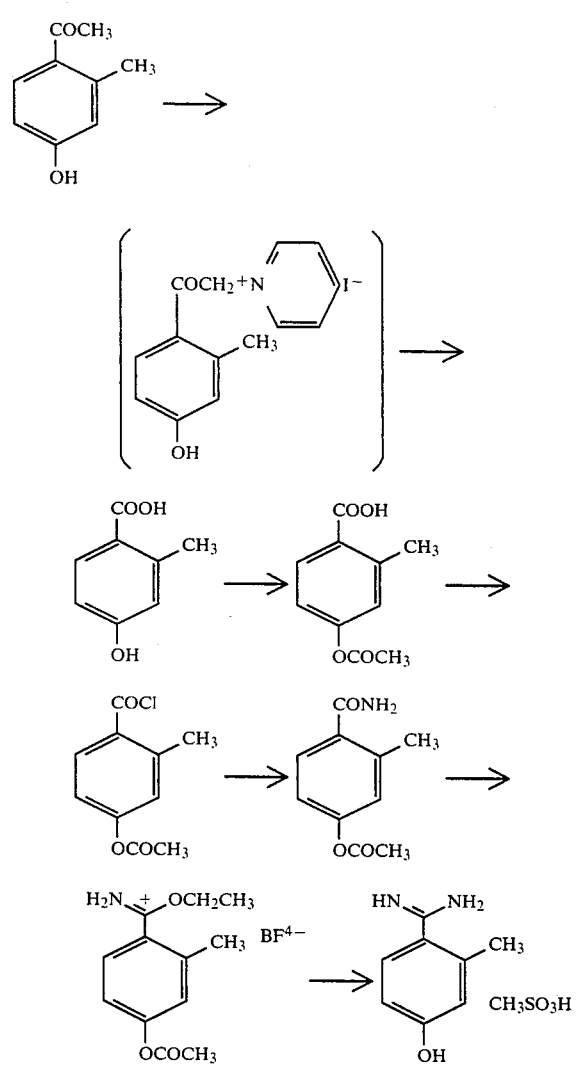

I. Synthesis of 4-hydroxy-2-methylbenzoic acid

Into 67 ml of pyridine, was dissolved 20 g of 4-hydroxy-2-methylacetophenone. After addition of 33.8 g of iodine, the solution was heated for 30 minutes on a boiling water bath and left standing overnight at room temperature. A pale brown solid precipitated from the reaction mixture was washed out of the reaction vessel with ethyl ether, then washed with water, and dried to obtain 38 g of an intermediate.

IR, $\nu_{max.}^{KBr}$, cm$^{-1}$: 3180, 1670.

In 1.9 liters of a 50% aqueous ethanol, was suspended 35.7 g of the above intermediate. To the suspension was added 38 g of sodium hydroxide. After having been heated for one hour on a boiling water bath, the reaction mixture was concentrated to half the volume and washed with ethyl acetate. The aqueous layer was acidified with concentrated hydrochloric acid and extracted with ethyl acetate. The organic layer was dried over anhydrous magnesium sulfate and freed from the solvent by distillation under reduced pressure to obtain 26.9 g of a pale brown oily substance. This oily substance was treated with an ethyl ether-petroleum ether mixture to yield 12.4 g of a pale brown solid.

IR, $\nu_{max.}^{KBr}$, cm$^{-1}$: 3380, 2950, 2600, 1655, 1600.

In 100 to 150 ml of methanol, was dissolved 12.1 g of the above solid and to the resulting solution was added 1.2 g of a 10% palladium-carbon. To the mixture, while being stirred at room temperature, was added carefully 9.5 g of sodium borohydride in small portions. After stirring for 30 minutes, the palladium-carbon was removed by filtration. The filtrate was concentrated under reduced pressure and admixed with water. The resulting aqueous solution was acidified with concentrated hydrochloric acid and extracted with ethyl ether. The organic layer was washed with a saturated aqueous sodium chloride solution, dried over anhdyrous magnesium sulfate, and freed from the solvent by distillation under reduced pressure. The residue was recrystallized from hot water to obtain 8.5 g of 4-hydroxy-2-methylbenzoic acid.

Melting point: 175°–177° C.

IR, $\nu_{max.}^{KBr}$, cm$^{-1}$: 3600–2000, 1665, 1600, 1575.

NMR, CD$_3$COCD$_3$, δ: 2.60 (3H, s), 6.77 (2H, m), 7.67 (2H, br), 8.00 (1H, d, J=9.0 Hz).

II. Synthesis of 4-acetyloxy-2-methylbenzoic acid

Into 40 ml of anhydrous ethyl ether, was dissolved 7.1 g of 4-hydroxy-2-methylbenzoic acid followed by 21.3 g of acetic anhydride. The solution was stirred for 2.4 hours at room temperature. The reaction mixture was freed from the solvent under reduced pressure. The residue was admixed with hot water, then allowed to cool, and extracted with ethyl ether. The organic layer was washed with 2% hydrochloric acid, dried over anhydrous magnesium sulfate, and freed from the solvent by distillation under reduced pressure. The residue was recrystallized from an ethyl ether-petroleum ether mixture to obtain 7.5 g of 4-acetyloxy-2-methylbenzoic acid.

Melting point: 136°–137.5° C.

IR, $\nu_{max.}^{KBr}$, cm$^{-1}$: 3250–2400, 1745, 1670, 1213.

NMR, CDCl$_3$, δ: 2.33 (3H, s), 2.70 (3H, s), 7.10 (2H, m), 8.17 (1H, d, J=9.0 Hz), 11.42 (1H, br).

III. Synthesis of 4-acetyloxy-2-methylbenzoyl chloride

In 60 ml of anhydrous ethyl ether, was suspended 6.2 g of 4-acetyloxy-2-methylbenzoic acid. To the suspension, was added 8.0 g of phosphorus pentachloride. The suspension was stirred for 3 hours at room temperature. The reaction mixture was freed from the solvent by distillation under reduced pressure, admixed again with ethyl ether, and freed from the solvent by distillation to obtain 4-acetyloxy-2-methylbenzoyl chloride.

IR, $\nu_{max.}^{neat}$, cm$^{-1}$: 1760, 1190.

IV. Synthesis of 4-acetyloxy-2-methylbenzamide

The acyl chloride prepared above was dissolved in 100 ml of anhydrous ethyl ether. Dried gaseous ammonia was introduced into the stirred solution and the stirring was continued for 20 to 30 minutes. The white crystals precipitated from the reaction mixture were collected by filtration, washed with ethyl ether, and dissolved in ethyl acetate. The resulting solution was washed with water, dried over anhydrous magnesium sulfate, and freed from the solvent by distillation under reduced pressure. The residue was washed with ethyl ether to obtain 4.9 g of white needle crystals of 4-acetyloxy-2-methylbenzamide.

mp: 169.5°–171° C.

IR, $\nu_{max.}^{KBr}$, cm$^{-1}$: 3360, 3175, 1750, 1650, 1215.

NMR, DMSO-d$_6$, δ: 2.23 (3H, s), 2.37 (3H, s), 7.00 (2H, m), 7.42 (1H, d, J=9.0 Hz), 7.13–7.90 (2H, br).

V. Synthesis of 4-iminoethoxymethyl-3-methylphenyl acetate hydrogen boron tetrafluoride To a stirred suspension of 3.9 g of 4-acetyloxy-2-methylbenzamide in 40 ml of anhydrous methylene chloride, was added slowly dropwise a solution of 3.8 g of Meerwein reagent [(C$_2$H$_5$)$_3$O$^+$BF$_4^-$] in 15 ml of anhydrous methylene chloride. To the reaction mixture which had been stirred for 24 hours at room temperature, was added a large volume of anhydrous ethyl ether. A white solid substance which was precipitated was collected by filtration and dried to obtain 5.8 g of 4-iminoethoxymethyl-3-methylphenyl acetate hydrogen boron tetrafluoride.

Melting point: 182°–184° C.

IR, $\nu_{max.}^{KBr}$, cm$^{-1}$: 3330, 3190, 2920, 1755, 1690, 1600, 1050.

NMR, DMSO-d$_6$, δ: 1.50 (3H, t, J=7.0 Hz), 2.32 (3H, s), 2.48 (3H, s), 4.65 (2H, q, J=7.0 Hz), 7.23 (2H, m), 7.73 (1H, d, J=9.0 Hz).

VI. Synthesis of 4-amidino-3-methylphenol methanesulfonate

To 100 ml of ethanol, was added 5.8 g of 4-iminoethoxymethyl-3-methylphenyl acetate hydrogen boron tetrafluoride. Into the mixture, while being stirred, was introduced gaseous ammonia. The mixture was heated under reflux for 4 to 5 hours. The reaction mixture was freed from the solvent by distillation under reduced pressure. To the residue, was added ethanol followed by methanesulfonic acid. After addition of a small volume of ethyl ether, the mixture was freed from the insoluble solids by filtration. The filtrate was freed from the solvent by distillation under reduced pressure, leaving behind a viscous oily substance which was crystallized by treating with an acetone-ethyl ether mixture to obtain 1.0 g of a white powder of 4-amidino-3-methylphenol methanesulfonate.

mp: 120°–122° C.

IR, $\nu_{max.}^{KBr}$, cm$^{-1}$: 3300, 3130, 1655, 1610, 1228, 1210, 1190.

NMR, DMSO-d$_6$, δ: 2.33 (3H, s), 2.43 (3H, s), 6.80 (2H, m), 7.30 (1H, d, J=9.0 Hz), 8.78–9.28 (4H, br), 9.67–10.67 (1H, br).

EXAMPLE 16a

Synthesis of 4-amidino-2-methoxyphenyl benzoate

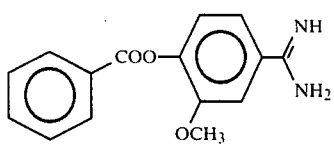

Compound No. 23

Into 100 ml of anhydrous pyridine, was dissolved 15.7 g of 4-amidino-2-methoxyphenol methanesulfonate. To the solution, while being cooled in and stirred, was added slowly 8.4 g of benzoyl chloride. After the addition, the mixture was stirred overnight at room temperature. The precipitate was separated by filtration and washed with pyridine. Ethyl ether was added to the filtrate to allow an oily substance to separate from the filtrate. The oily substance was washed 2 or 3 times with ethyl ether, then dissolved in water, and, while being stirred, admixed with a saturated aqueous sodium hydrogen carbonate solution to precipitate the carbonate of captioned compound. The carbonate was collected by filtration, washed with water, then with ethyl ether, and dried to obtain 20.7 g of the carbonate. The carbonate was suspended in 50 ml of methanol and, while being cooled in ice, admixed with 6.9 g of methanesulfonic acid. The crystals once dissolved and then precipitated again. After addition of ethyl ether, there were obtained 16.4 g of colorless granular crystals of 4-amidino-2-methoxyphenyl benzoate methanesulfonate.

EXAMPLE 16b

The 4-amidino-2-methoxyphenol methanesulfonate employed above was synthesized by the route as shown below:

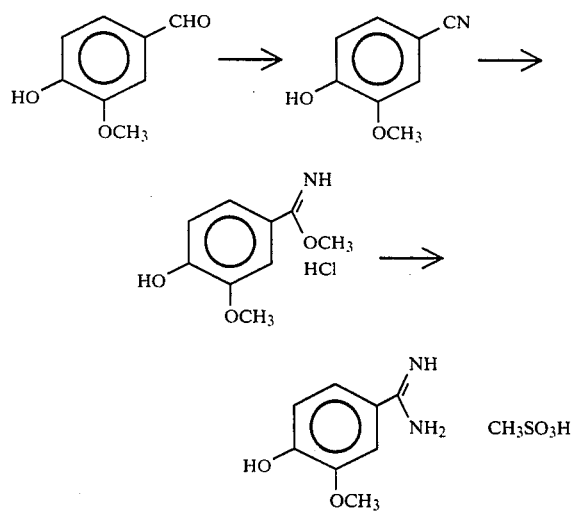

I. Synthesis of 4-cyano-2-methoxyphenol

This compound was synthesized by the Schmidt reaction [J.A.C.S., 70, 2293 (1948)] from 25.0 g of vanillin, 110 ml of concentrated sulfuric acid and 13.5 g of sodium azide. The yield of 4-cyano-2-methoxyphenol was 9.4 g.

mp: 84°–86° C. (89°–90° C., as reported in the literature).

IR, $\nu_{max}.^{KBr}$, cm$^{-1}$: 3360, 2220.

II. Synthesis of 4-methoxyiminomethyl-2-methoxyphenol

In 50 ml of anhydrous methanol, was dissolved 7.5 g of 4-cyano-2-methoxyphenol. The solution was saturated with dried gaseous hydrogen chloride, while being cooled in ice and stirred, and then stirred overnight at room temperature to precipitate yellow crystals. After addition of ethyl ether, the crystals were collected by filtration, washed with ethyl ether and dried to obtain 9.4 g of 4-methoxyiminomethyl-2-methoxyphenol hydrochloride.

mp: 123°–124.5° C.

IR, $\nu_{max}.^{KBr}$, cm$^{-1}$: 2920, 1680.

NMR, DMSO-d$_6$ δ: 3.90 (3H, s), 4.30 (3H, s), 7.07 (1H, d, J=8.5 Hz), 7.68 (1H, d, d, J=8.5, 2.0 Hz), 7.90 (1H, d, J=2.0 Hz), 6.80–8.00 (1H, br), 11.23–12.00 (1H, br).

III. Synthesis of 4-amidino-2-methoxyphenol

To a mixture of 100 ml of anhydrous methanol and about 50 ml of liquid ammonia, was added slowly 8.7 g of 4-methoxyiminomethyl-2-methoxyphenol hydrochloride. The mixture was stirred overnight at room temperature. The colorless crystals precipitated from the reaction mixture were collected by filtration, washed thoroughly with methanol, and dried to obtain 7.4 g of 4-amidino-2-methoxyphenol.

mp: >240° C.

IR, $\nu_{max}.^{KBr}$, cm$^{-1}$: 3300, 2800, 1680.

Then, to a suspension of 6.6 g of 4-amidino-2-methoxyphenol in 20 ml of methanol, was added 4.7 g of methanesulfonic acid. After the crystals had been dissolved, forming a uniform solution, ethyl ether was added to the solution and stirred, while cooling in ice, to obtain colorless crystals. After recrystallization from ethanol, there were obtained 8.1 g of prismatic crystals of 4-amidino-2-methoxyphenol methanesulfonate.

mp: 151°–152° C.

IR, $\nu_{max}.^{KBr}$, cm$^{-1}$: 3500–2800 (several lines), 1660, 1600, 1190.

NMR, DMSO-d$_6$, δ: 2.47 (3H, s), 3.90 (3H, s), 7.00 (1H, d, J=8.5 Hz), 7.43 (2H, m), 8.67–9.33 (4H, br), 10.27 (1H, br, s).

EXAMPLE 17a

Synthesis of 4-amidino-2-carboxyphenyl benzoate

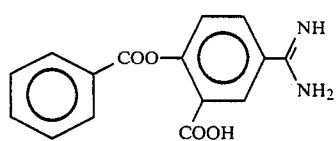

Compound No. 24

To a suspension of 3.0 g of 5-amidinosalicylic acid methanesulfonate in 40 ml of dried pyridine, while being cooled in ice and stirred, was added slowly 1.5 g of benzoyl chloride. The mixture was stirred for 3 hours at room temperature. The crystals gradually dissolved, forming a clear pale yellow solution, and an oily substance separated out. After addition of ethyl ether to the reaction mixture and removal of the supernatant, the oily substance was washed several times with ethyl ether and dissolved in water. Upon addition of a saturated aqueous sodium hydrogencarbonate solution, pale yellow crystals precipitated. After cooling in ice, the crystals were collected by filtration, washed with a small volume of water, and dried to obtain 1.0 g of the crystals. The crystals were suspended in a small volume of methanol and allowed to dissolve by the addition of 0.4 g of methanesulfonic acid. Ethyl ether was added to the solution with stirring to obtain 0.8 g of a colorless powder of 4-amidino-2-carboxyphenyl benzoate methanesulfonate.

EXAMPLE 17b

The 5-amidinosalicylic acid methanesulfonate employed above was synthesized as shown in the following reaction scheme:

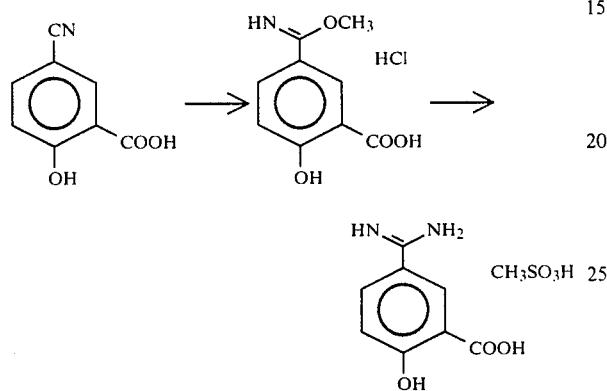

I. Synthesis of 5-methoxyiminomethylsalicylic acid

A solution of 6.0 g of 5-cyanosalicylic acid in 60 ml of anhydrous methanol, while being cooled in ice and stirred, was saturated with dried gaseous hydrogen chloride and stirred overnight at room temperature. Anhydrous ethyl ether was added to the reaction mixture to obtain 4.3 g of white crystals of 5-methoxyiminomethylsalicylic acid hydrochloride.

Melting point: 282°–284° C. (decomp.).

IR, $\nu_{max}^{KBr}$, cm$^{-1}$: 3280, 2970, 2720, 1660.

NMR, DMSO-d$_6$, δ: 3.07 (3H, s), 7.02 (1H, d, J=8.5 Hz), 8.07 (1H, d, d, J=8.5, 2.0 Hz), 8.42 (1H, d, J=2.0 Hz), 6.87–8.67 (2H, br), 10.13–11.33 (2H, br).

II. Synthesis of 5-amidinosalicylic acid

To a mixture of 40 ml of methanol and 20 ml of liquid ammonia, was added 4.0 g of 5-methoxyiminomethylsalicylic acid hydrochloride. The mixture was stirred overnight at room temperature. A colorless gelatinous substance precipitated from the reaction mixture was washed with methanol, and washed with a water-acetone (20 ml–80 ml) mixture to obtain 2.6 g of 5-amidinosalicylic acid.

IR, $\nu_{max}^{KBr}$, cm$^{-1}$: 3370, 3050, 1700, 1615.

To a suspension of 2.5 g of the 5-amidinosalicylic acid, was added 1.7 g of methanesulfonic acid followed by ethyl ether to obtain 3.5 g of 5-amidinosalicylic acid methanesulfonate.

mp: ~260° C. (decomp.).

IR, $\nu_{max}^{KBr}$, cm$^{-1}$: 3600–2700, 1650.

NMR, DMSO-d$_6$ δ: 2.43 (3H, s), 7.17 (1H, d, J=8.5 Hz), 7.98 (1H, d, d, J=8.5, 2.0 Hz), 8.37 (1H, d, J=2.0 Hz), 8.77–9.46 (4H, br), 10.20–11.17 (2H, br).

EXAMPLE 18a

Synthesis of 4-amidino-2-methoxycarbonylphenyl benzoate

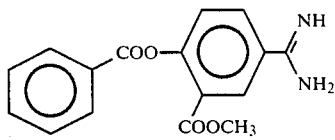

Compound No. 25

Into 40 ml of anhydrous pyridine, was dissolved 4.0 g of methyl 5-amidinosalicylate methanesulfonate. To the solution, while being cooled in ice and stirred, was added 1.9 g of benzoyl chloride. The mixture was stirred overnight at room temperature. The precipitate which was formed was separated by filtration and washed with pyridine. Ethyl ether was added to the filtrate and after a while colorless crystals precipitated. The crystals were collected by filtration, washed with ethyl ether and dissolved in water. A saturated aqueous sodium hydrogencarbonate solution was added to the solution while stirring. The precipitated colorless crystals were collected by filtration, washed with water, then with acetone, and dried to obtain 3.8 g of the carbonate of the captioned compound. To a suspension of the carbonate in a small volume of methanol, was added 1.2 g of methanesulfonic acid. The carbonate dissolved with effervescence and immediately thereafter colorless crystals precipitated. The crystals were recrystallized from a methanol-ethyl ether mixture to obtain 4.1 g of colorless needle crystals of 4-aminido-2-methoxycarbonylphenyl benzoate methanesulfonate.

EXAMPLE 18b

The methyl 5-amidinosalicylate methanesulfonate employed above was synthesized according to the following reaction scheme:

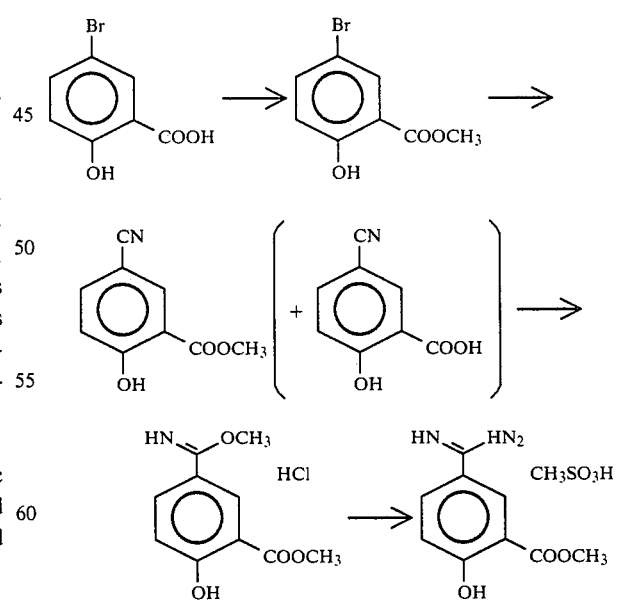

I. Synthesis of methyl 5-bromosalicylate

Into 400 ml of anhydrous methanol, was dissolved 96.0 g of 5-bromosalicylic acid. After addition of 20 ml of concentrated sulfuric acid, the mixture was heated under reflux for about 20 hours. The reaction mixture was freed from the solvent, allowed to cool, and extracted by adding water and ethyl ether. The organic layer was washed with water, then twice with a saturated aqueous sodium hydrogencarbonate solution, and finally with a saturated sodium chloride solution. The washed organic layer was dried over magnesium sulfate, freed from the solvent by distillation under reduced pressure to obtain 93.7 g of colorless crystals of methyl 5-bromosalicylate.

mp: 48°–50° C.

IR, $\nu_{max}.^{KBr}$, cm$^{-1}$: 3170, 1675.

II. Synthesis of methyl 4-cyanosalicylate

To a mixture of 92.0 g of methyl 4-bromosalicylate and 42.8 g of cuprous cyanide, was added 90 ml of DMF. While being stirred vigorously under a nitrogen stream, the mixture was heated at an oil bath temperature of 160° to 170° C. for 2 to 3 hours. The reaction mixture was allowed to cool and the green solid was added to water to be finely disintegrated. The disintegrated solid was collected by filtration and washed thoroughly with water. The resulting product was extracted several times with aqueous ammonia (concentrated ammonia:water=1:5). The aqueous ammonia layers were combined and, while being cooled in ice, acidified with 10% hydrochloric acid to obtain colorless crystals. The crystals were collected by filtration, washed with water, dissolved in ethyl acetate, washed twice with water, then three times with a 2% aqueous sodium hydrogencarbonate solution, and finally with a saturated aqueous sodium chloride solution. The organic layer was dried over magnesium sulfate and freed from the solvent by distillation to obtain colorless crystals which were recrystallized from ethanol, yielding 45.0 g of colorless needle crystals of methyl 5-cyanosalicylate.

mp: 114°–115° C.

IR, $\nu_{max}.^{KBr}$, cm$^{-1}$: 3070, 2220, 1665.

NMR, CDCl$_3$, δ: 4.03 (3H, s), 7.13 (1H, d, J=9.0 Hz), 7.93 (1H, d, d, J=9.0, 2.0 Hz), 8.23 (1H, d, J=2.0 Hz).

On the other hand, the alkaline layer was acidified with 10% hydrochloric acid to precipitate colorless crystals which were recrystallized from aqueous ethanol, yielding 6.6 g of colorless needle crystals of 5-cyanosalicylic acid.

mp: ~173° C. (decomp.).

IR, $\nu_{max}.^{KBr}$, cm$^{-1}$: 3520, 3470, 3200, ~2250, 2240, 1680.

III. Synthesis of methyl 5-methoxyiminomethylsalicylate

In 450 ml of anhydrous methanol, was suspended 44.0 g of methyl 5-cyanosalicylate. While being cooled in ice and stirred, the suspension was saturated with dried gaseous hydrogen chloride. The suspension was further stirred for 2 days at room temperature, then the resulting solution was concentrated to about 200 ml at a low temperature under reduced pressure, and admixed with ethyl acetate to precipitate colorless crystals. The crystals were collected by filtration and dried to obtain 41.0 g of methyl 5-methoxyiminomethylsalicylate hydrochloride.

IR, $\nu_{max}.^{KBr}$, cm$^{-1}$: 3170, 1690, 1630.

NMR, DMSO-d$_6$ δ: 3.08

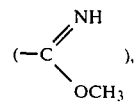

3.93 (—COOCH$_3$), 7.07 (d, J=8.5 Hz), 8.12 (d, d, J=8.5, 2.5 Hz), 8.38 (d, J=2.5 Hz).

IV. Synthesis of methyl 5-amidinosalicylate

To a solution prepared by introducing 6.0 g of dried gaseous ammonia into 200 ml of anhydrous methanol, was added with stirring at room temperature 40.0 g of methyl 5-methoxyiminomethylsalicylate hydrochloride. The crystals dissolved, yielding a clear yellow solution and after 5 to 10 minutes there occurred precipitation of colorless crystals. The crystals were collected by filtration and washed with methanol to obtain 16.8 g of methyl 5-amidinosalicylate.

mp: 226°–229° C. (decomp.).

IR, $\nu_{max}.^{KBr}$, cm$^{-1}$: 3360, 3200, 1665.

In 100 ml of methanol, was suspended 16.0 g of the methyl 5-amidinosalicylate. To the suspension was added 10.3 g of methanesulfonic acid to dissolve the crystals. Ethyl ether was added to the resulting solution, while being cooled in ice and stirred, to obtain 23.0 g of colorless needle crystals of methyl 5-amidinosalicylate methanesulfonate.

mp: 156°–159° C.

IR, $\nu_{max}.^{KBr}$, cm$^{-1}$: 3300, 3050, 1650, 1200.

NMR, DMSO-d$_6$, δ: 2.47 (3H, s), 3.93 (3H, s), 7.22 (1H, d, J=8.5 Hz), 8.02 (1H, d, d, J=8.5, 2.0 Hz), 8.32 (1H, d, J-2.0 Hz), 8.79–9.48 (4H, br), 11.17 (1H, br).

EXAMPLE 19

Synthesis of 4-amidino-2-chlorophenyl benzoate

Compound No. 26

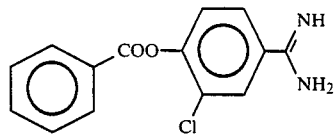

To 30 ml of anhydrous pyridine, was added 2.7 g of 4-amidino-2-chlorophenol methanesulfonate. To the mixture, while being cooled in ice, was added 1.4 g of benzoyl chloride. The mixture was stirred for 30 minutes, while being cooled in ice, then for 5 hours at room temperature. The reaction mixture was mixed with 100 ml of ethyl ether to allow an oily substance to separate out. The oily substance was dissolved in 20 ml of methanol and poured into a saturated aqueous sodium hydrogencarbonate solution. The precipitated crystals were collected by filtration and washed with water, then with acetone. The washed crystals were added to 20 ml of methanol and admixed with 2.5 g of methanesulfonic acid. The insolubles were removed by filtration and 100 ml of ethyl ether was added to the filtrate. The precipitated colorless crystals were collected by filtration to obtain 2.5 g of 4-amidino-2-chlorophenyl benzoate methanesulfonate.

EXAMPLE 19b

The 4-amidino-2-chlorophenol methanesulfonate employed above was synthesized according to the following reaction scheme:

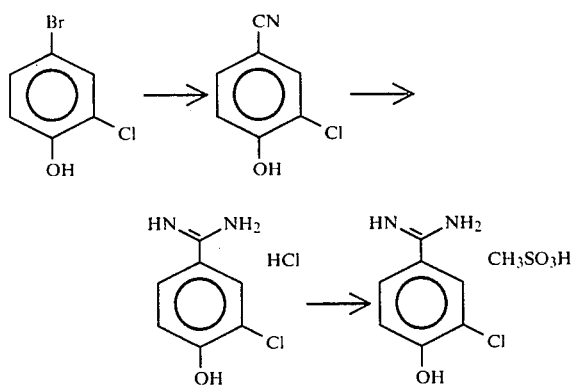

I. Synthesis of 2-chloro-4-cyanophenol

To 10 ml of DMF, were added 9.0 g of 2-chloro-4-bromophenol and 4.7 g of cuprous cyanide (CuCN). The resulting solution was heated at 160° c. for 2 hours while passing nitrogen through the solution. The reaction mixture was allowed to cool, admixed with 100 ml of a 10% aqueous sodium hydroxide solution, and thoroughly stirred. The insolubles were removed by filtration and the filtrate was neutralized with 10% hydrochloric acid. The precipitate was collected by filtration to obtain 4.7 g of pale yellow crystals of 2-chloro-4-cyanophenol.

mp: 110°–113° C.

IR, $\nu_{max}^{KBr}$, cm$^{-1}$: 3220, 2240, 1600, 1307.

II. Synthesis of 2-chloro-4-methoxyiminomethylphenol hydrochloride

While being cooled in ice, a solution of 4.5 g of 2-chloro-4-cyanophenol in 50 ml of methanol was saturated with dried gaseous hydrogen chloride (HCl). The solution was left standing overnight at room temperature and mixed with 100 ml of ethyl ether to precipitate crystals which were collected by filtration to obtain 4.0 g of 2-chloro-4-methoxyiminomethylphenol hydrochloride.

mp: 138°–139° C.

IR, $\nu_{max}^{KBr}$, cm$^{-1}$: 3010, 1680, 1600, 1060.

NMR, DMSO-d$_6$, δ: 3.05 (3H, s), 5.0–6.0 (b), 7.03–8.23 (3H, m).

III. Synthesis of 4-amidino-2-chlorophenol methanesulfonate

Anhydrous gaseous ammonia (NH$_3$) was passed through a mixture of 3.5 g of 2-chloro-4-methoxyiminomethylphenol hydrochloride and 50 ml of anhydrous methanol. The mixture was stirred overnight at room temperature and freed from the solvent by distillation. The residue was dissolved in 20 ml of methanol and mixed with 2.5 g of methanesulfonic acid followed by 100 ml of ethyl ether to obtain 3.0 g of 4-amidino-2-chlorophenol methanesulfonate in colorless oily form.

EXAMPLE 20a

Synthesis of 4-amidino-2-nitrophenyl benzoate

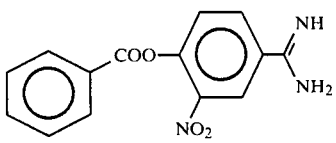

Compound No. 27

Into 40 ml of dried pyridine, was dissolved 4.2 g of 4-amidino-2-nitrophenol methanesulfonate. To the solution, while being cooled in ice and stirred, was added portionwise 2.1 g of benzoyl chloride. The solution was stirred overnight at room temperature and removed of the insolubles by filtration. Ethyl ether was added to the filtrate to allow an oily substance to separate out. After removal of the supernatant, the oily substance was washed a few times with ethyl ether, and dissolved in water. To the aqueous solution, while being stirred, was added a saturated aqueous sodium hydrogencarbonate solution to precipitate the carbonate of the captioned compound. The carbonate precipitate was collected by filtration, washed with water, then with acetone, and dried to obtain 4.0 g of pale yellow crystals. To the carbonate crystals suspended in 10 ml of methanol, was added 1.4 g of methanesulfonic acid. The mixture turned, with effervescence, into a homogeneous solution. Upon addition of ethyl ether there were obtained 4.1 g of colorless granular crystals of 4-amidino-2-nitrophenyl benzoate methanesulfonate.

EXAMPLE 20b

The 4-amidino-2-nitrophenol methanesulfonate used above was synthesized in the following manner:

To 20 ml of concentrated sulfuric acid, was added 7.6 g of 4-amidinophenol hydrochloride. When the evolution of hydrogen chloride gas had ceased, the solution was cooled in an ice-salt bath and 3.0 ml of nitric acid was slowly added to the solution while being stirred. The mixture was then stirred at room temperature for 20 to 30 minutes. The reaction mixture, orange in color, was diluted by pouring into a large volume of ice water. The diluted solution was added in small portions to a saturated aqueous sodium hydrogencarbonate solution to precipitate orange needle crystals. The crystals were collected by filtration and dried to obtain 7.6 g of 4-amidino-2-nitrophenol.

mp: >240° C.

IR, $\nu_{max}^{KBr}$, cm$^{-1}$: 3600–2800, 1650, 1610, 1490, 1275.

In 20 ml of methanol, was suspended 7.3 g of the 4-amidino-2-nitrophenol obtained above. To the suspension was added 5.8 g of methanesulfonic acid. When the crystals had dissolved forming a homogeneous solution, ethyl ether was added to the solution, and the solution was stirred while cooling in ice to precipitate pale yellow crystals which were recrystallized from ethanol, yielding 9.8 g of pale yellow granular crystals of 4-amidino-2-nitrophenol methanesulfonate.

mp: 158°–159.5° C.

IR, $\nu_{max}^{KBr}$, cm$^{-1}$: 3380, 3050, 1665, 1620, 1190, 1180.

NMR, DMSO-d$_6$, δ: 2.48 (3H, s), 7.38 (1H, d, J=8.5 Hz), 8.07 (1H, d, d, J=8.5, 2.0 Hz), 8.48 (1H, d, J=2.0 Hz), 9.00–9.53 (4H, br).

EXAMPLE 21a

Synthesis of 5-amidino-2-benzoyloxybenzenesulfonic acid

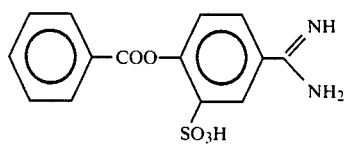

Compound No. 28

To 30 ml of dried pyridine, was added 3.0 g of 5-amidino-2-hydroxybenzenesulfonic acid. To the mixture, while being cooled in ice, was slowly added dropwise 2.0 g of benzoyl chloride. After the addition, the mixture was stirred overnight at room temperature. The insolubles deposited from the reaction mixture were separated by filtration, washed with pyridine, then with water, finally with acetone, and suspended in methanol. The insolubles were removed by filtration, and ethyl ether was added to the filtrate to precipitate a colorless solid. The solid was collected by filtration and recrystallized from a methanol-ethyl ether mixture to obtain 5-amidino-2-benzoyloxybenzenesulfonic acid in colorless solid form.

EXAMPLE 21b

The 5-amidino-2-hydroxybenzenesulfonic acid employed above was obtained in the following manner.

To 15 ml of 60% fuming sulfuric acid, while being cooled in ice, was added slowly 10.0 g of 4-amidinophenol hydrochloride. After the addition, the mixture was stirred at room temperature for 4 hours, then poured slowly into 200 ml of ice water, and stirred for a while. The colorless solid which was precipitated was collected by filtration, washed with water, then with acetone, and dried to obtain 10.2 g of 5-amidino-2-hydroxybenzenesulfonic acid.

mp: >300° C.

IR, $\nu_{max}^{KBr}$, cm$^{-1}$: 3600–2600, 1670, 1610, 1230, 1165.

NMR, NaOD, δ: 6.81 (1H, d, J=9.0 Hz), 7.64 (1H, d, d, J=9.0, 3.0 Hz), 8.13 (1H, d, J=3.0 Hz).

EXAMPLE 22a

Synthesis of 4-amidino-2-benzoylphenyl benzoate

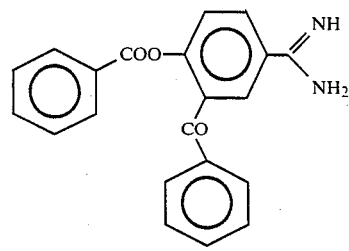

Compound No. 29

Into 10 ml of dried pyridine, was dissolved 1.0 g of 4-amidino-2-benzoylphenol methanesulfonate. To the solution, while being cooled in ice and stirred, was added dropwise 422 mg of benzoyl chloride. The mixture was then stirred at room temperature for 3 hours. The reaction mixture was freed from insolubles by filtration and ethyl ether was added to the filtrate to throw out an oily substance. The oily substance was dissolved in water, and the resulting aqueous solution was added to a saturated aqueous sodium hydrogencarbonate solution, while being cooled in ice and stirred. The precipitated white crystals were collected by filtration, washed with water, then with acetone, and dried to obtain 854 mg of 4-amidino-2-benzoylphenyl benzoate carbonate.

IR, $\nu_{max}^{KBr}$, cm$^{-1}$: 3375, 3025, 2625, 1730, 1655, 1600.

To a suspension of 854 mg of the above carbonate in a small volume of methanol, was added 242 mg of methanesulfonic acid to form a homogeneous solution. Ethyl ether was added to the solution and triturated while cooling in ice to obtain 920 mg of a white powder of 4-amidino-2-benzoylphenyl benzoate methanesulfonate.

mp: ~160° C.

IR, $\nu_{max}^{KBr}$, cm$^{-1}$: 3275, 3100, 1730, 1675, 1650.

NMR, DMSO-d$_6$, δ: 2.48 (3H, s), 7.25–8.33 (13H, m), 9.21–9.71 (4H, br).

EXAMPLE 22b

The 4-amidino-2-benzoylphenol methanesulfonate employed above was synthesized according to the following reaction scheme:

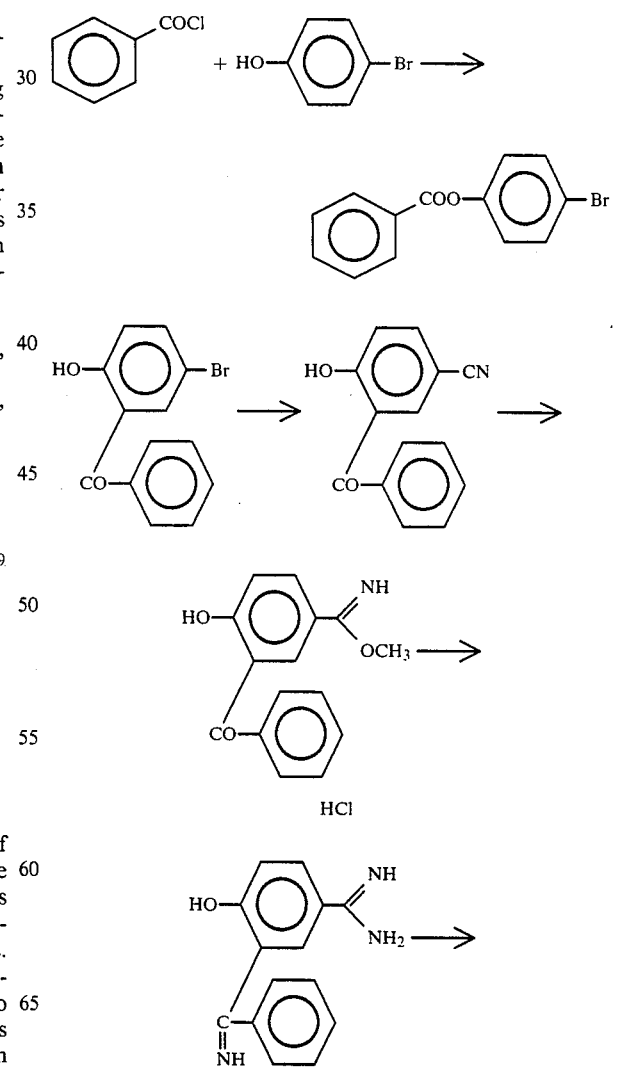

-continued

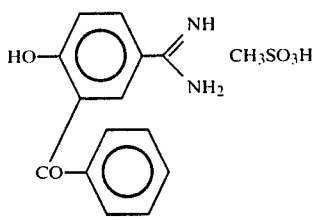

I. Synthesis of 4-bromophenyl benzoate

To a solution of 360 g of 4-bromophenol in 4.3 liters of ethyl acetate, was added 326 ml of triethylamine. To the mixture, while being cooled in ice and stirred, was added dropwise 300 g of benzoyl chloride over a period of 90 minutes. After two hours of stirring, water was added to the reaction mixture to remove the triethylamine hydrochloride. The ethyl acetate layer was washed successively with a dilute aqueous alkali solution, dilute hydrochloric acid, and saturated aqueous sodium chloride solution, then dried over anhydrous magnesium sulfate, and freed from the solvent by distillation. The residue was washed with ethanol and dried to obtain 500 g of 4-bromophenyl benzoate.

mp: 98°–100° C.

IR, $\nu_{max}^{KBr}$, cm$^{-1}$: 1730. NMR, CDCl$_3$, δ: 7.08 (2H, d, J=9.0 Hz), 7.50 (5H, m), 8.15 (d, d, J=8.0, 3.0 Hz).

II. Synthesis of 2-benzoyl-4-bromophenol

An intimate mixture was prepared from 500 g of 4-bromophenyl benzoate and 317 g of anhydrous aluminum chloride by grinding together in a mortar. The mixture was gradually heated with stirring to form a homogeneous solution. The temperature of the solution was further elevated to a level of 140°–150° C. and kept at this level for 15 to 20 minutes. After having been left to cool down, the reaction mixture was carefully added with stirring to a mixture of 2.6 kg of ice and 1.3 liters of concentrated hydrochloric acid. The precipitated yellow crystals were collected by filtration, washed with water, and shaken together with a 10% aqueous potassium hydroxide solution and ethyl ether. The alkali layer was acidified with concentrated hydrochloric acid to precipitate yellow crystals which were recrystallized from ethanol, giving 373 g of yellow needle crystals of 2-benzoyl-4-bromophenol.

mp: 109°–110° C.

IR, $\nu_{max}^{KBr}$, cm$^{-1}$: 3050, 1618, 1595.

NMR, CDCl$_3$, δ: 6.97 (1H, d, J=8.0 Hz), 7.57 (7H, m), 11.92 (1H, br-s).

III. Synthesis of 2-benzoyl-4-cyanophenol

To a mixture of 370 g of 2-benzoyl-4-bromophenol and 146 g of cuprous cyanide, was added 370 ml of DMF. The mixture was refluxed for 4 hours, while being stirred vigorously under a nitrogen stream. After having been left cooling down, the reaction mixture was poured into ice water. The precipitated solid matter was dissolved in a 10% aqueous sodium hydroxide solution, removed of the insolubles by filtration, and acidified with concentrated hydrochloric acid to obtain a yellow solid substance. This substance was dissolved in ethanol, freed from the insolubles, admixed with water to precipitate crystals which were dried, yielding 214 g of yellow crystals of 2-benzoyl-4-cyanophenol.

mp: 106°–108° C.

IR, $\nu_{max}^{KBr}$, cm$^{-1}$: 3050, 2220, 1620, 1590.

NMR, CDCl$_3$, δ: 7.63 (8H, br-s).

Mass spectrum, m/e: 223 (M$^+$).

IV. Synthesis of 2-benzoyl-4-methoxyiminomethylphenol hydrochloride

A suspension of 214 g of 2-benzoyl-4-cyanophenol in 1.7 liters of anhydrous methanol was saturated with anhydrous hydrogen chloride, while being cooled in ice and stirred. After having been stirred overnight at room temperature, the mixture was mixed with a large volume of ethyl ether. The precipitated crystals were collected by filtration and dried to yield 156 g of 2-benzoyl-4-methoxyiminomethylphenol hydrochloride.

mp: 131°–132° C.

IR, $\nu_{max}^{KBr}$, cm$^{-1}$: 3000, 1655, 1600.

NMR, 60 MC, DMSO-d$_6$, δ (ppm): 3.05 (s), 6.97–8.33 (m), 10.33–11.33 (br).

V. Synthesis of 4-amidino-2-phenyliminomethylphenol

In one liter of anhydrous methanol, was suspended 156 g of 2-benzoyl-4-methoxyiminomethylphenol hydrochloride. While stirring and introducing gaseous ammonia, the suspension was heated at 60° C. for 2 to 3 hours. After removal of the solvent by distillation, the residue was dissolved in a saturated aqueous sodium hydrogencarbonate solution and triturated while being cooled in ice, to precipitate yellow crystals. The crystals were thoroughly washed with water, then with acetone, and dried to obtain 125 g of 4-amidino-2-phenyliminomethylphenol carbonate.

IR, $\nu_{max}^{KBr}$, cm$^{-1}$: 3325, 3050, 1655, 1595.

VI. Synthesis of 4-amidino-2-benzoylphenol methanesulfonate

Into one liter of 3N hydrochloric acid, was dissolved 125 g of 4-amidino-2-phenyliminomethylphenol carbonate. The solution was heated for one hour on a boiling water bath. The reaction mixture was cooled in ice to precipitate white crystals. The crystals were collected by filtration, removed thoroughly of adhered water, washed with an acetone-ethyl ether mixture, and dried to obtain 4-amidino-2-benzoylphenol hydrochloride.

mp: 219°–224° C.

IR, $\nu_{max}^{KBr}$, cm$^{-1}$: 3350, 3100, 1668, 1632, 1600.

In 200 ml of methanol, was suspended the 4-amidino-2-benzoylphenol hydrochloride obtained above. To the suspension was added 60 g of methanesulfonic acid followed by ethyl ether. The precipitated pale yellow crystals were collected by filtration and dried to obtain 109 g of 4-amidino-2-benzoylphenol meethanesulfonate.

mp: 186°–189° C.

(The yield based on 4-bromophenol was 15.2%)

IR, $\nu_{max}^{KBr}$, cm$^{-1}$: 3500, 3280, 3100, 1675, 1630, 1600, 1200.

NMR, DMSO-d$_6$, δ: 2.74 (3H, s), 7.20 (1H, d, J=8.0 Hz), 7.40–8.10 (8H, m), 8.86–9.36 (4H, br).

EXAMPLE 23a

Synthesis of 4-amidino-2-benzoylaminophenyl benzoate

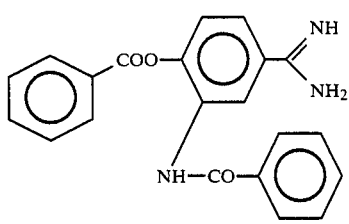

Compound No. 30

Into 30 ml of pyridine, was dissolved 1.7 g of 4-amidino-2-aminophenol dimethanesulfonate. To the solution, while being cooled in ice and stirred, was added 1.8 g of benzoyl chloride. The mixture was stirred for 30 minutes while cooling in ice and 2 hours at room temperature. The reaction mixture was admixed with about 100 ml of ethyl ether to allow a colorless oily substance to separate out. The solvent was removed by decantation and the residue was dissolved in a small volume of ethanol. Upon addition of a saturated aqueous sodium hydrogencarbonate solution, colorless crystals of 4-amidino-2-benzoylaminophenyl benzoate carbonate were precipitated. The crystals were collected by filtration, washed with water, then with acetone, and suspended in ethanol. On addition of methanesulfonic acid, the suspension turned into a clear solution. Ethyl ether was added to the solution to precipitate crystals. The crystals were collected by filtration and recrystallized from an ethanol-ethyl ether mixture to obtain 1.4 g of colorless crystals of 4-amidino-2-benzoylaminophenyl benzoate methanesulfonate.

EXAMPLE 23b

The 4-amidino-2-aminophenol dimethanesulfonate employed above was synthesized in the following manner:

To 200 ml of ethanol, were added 15 g of 4-amidino-2-nitrophenol methanesulfonate and 1 g of a 10% palladium-carbon. While introducing hydrogen, the mixture was vigorously stirred until no more hydrogen had been absorbed (about 3700 ml of hydrogen were absorbed). The reaction mixture was removed of the insolubles and concentrated to about 50 ml. To the concentrate was added 6.2 g of methanesulfonic acid followed by 200 ml of ethyl ether. The precipitated crystals were collected by filtration to obtain 13 g of 4-amidino-2-aminophenyl dimethanesulfonate.

mp: 195°–197° C.

IR, $\nu_{max}^{KBr}$, cm$^{-1}$: 3700–2800, 1665, 1625, 1190, 1040.

NMR, DMSO-d$_6$, δ: 2.40 (6H, s), 7.07–7.60 (m), 8.73–9.33 (4H, br).

EXAMPLE 24

Synthesis of 4-amidino-2-methoxyphenyl cinnamate

Compound No. 31

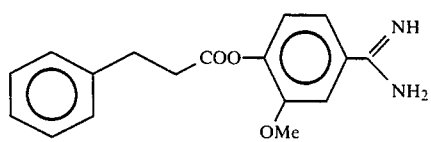

To a solution of 6.2 g of 4-amidino-2-methoxyphenol methanesulfonate in 30 ml of dried pyridine, while being cooled in ice and stirred, was added 3.9 g of cinnamoyl chloride. Immediately after the addition a colorless solid substance precipitated from the reaction mixture. After 3 hours of stirring at room temperature, ethyl ether was added to the mixture and the precipitate was collected by filtration. The precipitate was dissolved in methanol and mixed with a saturated aqueous sodium bicarbonate solution to precipitate a white gelatinous substance. The gelatinous substance was collected by filtration, washed with water, then with acetone and dried to obtain 6.3 g of the carbonate of the captioned compound. Upon addition of 2.3 g of methanesulfonic acid to the carbonate suspended in 60 ml of methanol, a change in crystal form of the carbonate took place accompanied by effervescence. The suspension was heated to dissolve the crystals and then cooled to obtain 6.3 g of colorless needle crystals of 4-amidino-2-methoxyphenyl cinnamate methanesulfonate.

EXAMPLE 25

Synthesis of 4-amidino-2-methoxyphenyl 3-phenylpropionate

Compound No. 32

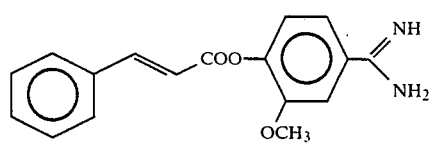

(a) Into 50 ml of dried pyridine, was dissolved 1.5 g of 3-phenylpropionic acid. After addition of 3.1 g of DCC, the mixture was stirred for 30 minutes, then admixed with 2.62 g of 4-amidino-2-methoxyphenol methanesulfonate and stirred overnight. The reaction mixture was freed from insolubles by filtration and admixed with ethyl ether. The precipitate which was formed was recrystallized from ethanol to obtain 2.7 g of colorless prismatic crystals of 4-amidino-2-methoxyphenyl 3-phenylpropionate methanesulfonate.

(b) To 100 ml of methanol, were added 2.0 g of 4-amidino-2-methoxyphenyl cinnamate methanesulfonate and 0.5 g of a 10% palladium-carbon. Hydrogen was fed to the mixture which was stirred vigorously to facilitate absorption. The reaction mixture was freed from the insolubles by filtration and from the solvent by distillation. The residue was recrystallized from ethanol to obtain 1.5 g of the same 4-amidino-2-methoxyphenyl 3-phenylpropionate methanesulfonate.

EXAMPLE 26

The following compounds were obtained by the procedures similar to those of Examples 15 to 25:

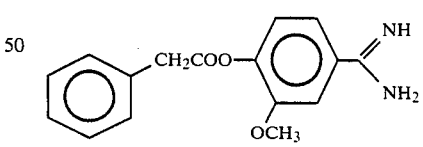

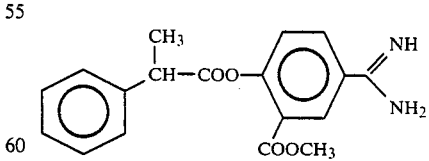

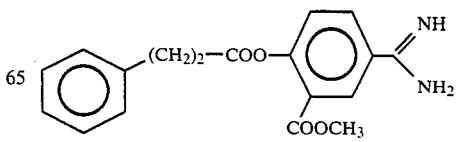

Compound No. 33
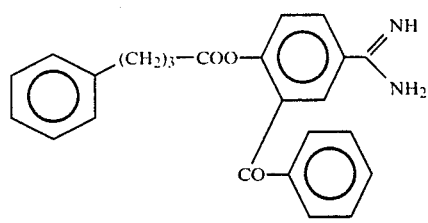
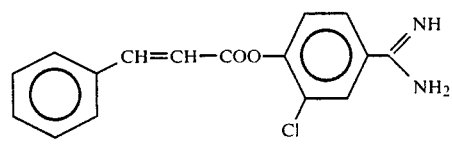
Compound No. 34
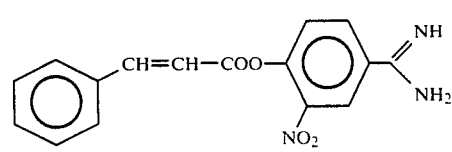
Compound No. 35
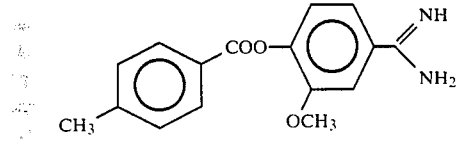
Compound No. 36
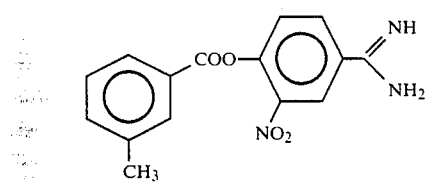
Compound No. 37
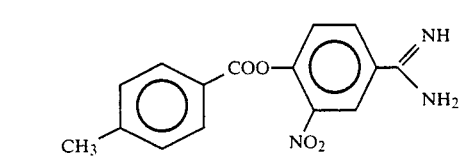
Compound No. 38
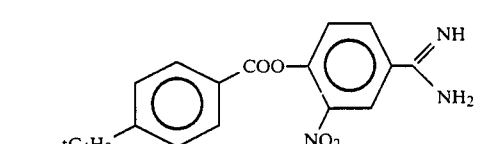
Compound No. 39
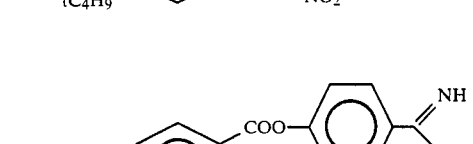
Compound No. 40
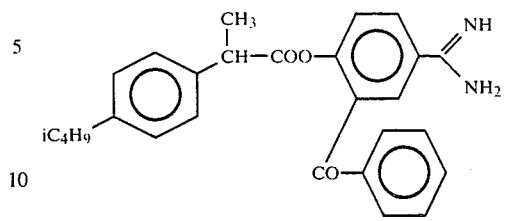
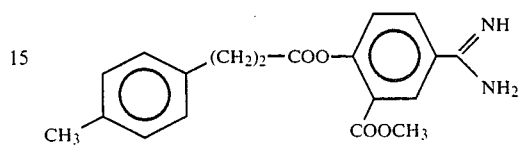
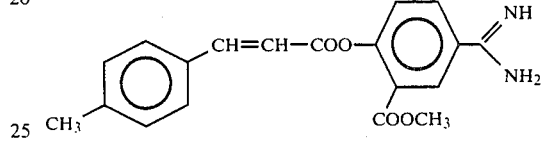
Compound No. 41
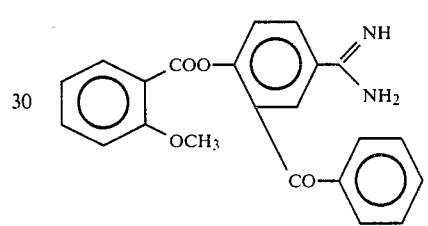
Compound No. 42
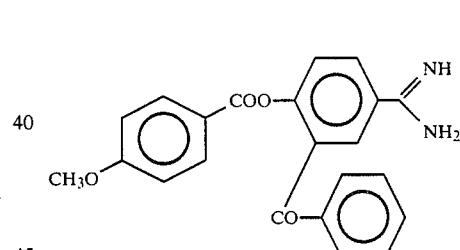
Compound No. 43
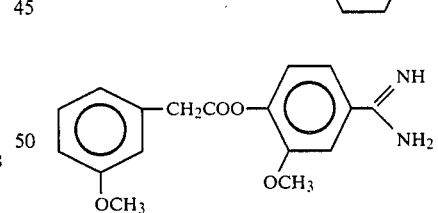
Compound No. 44
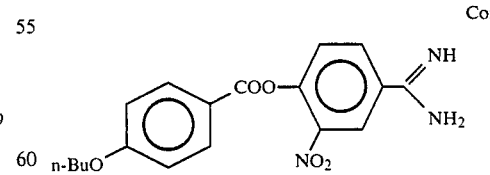
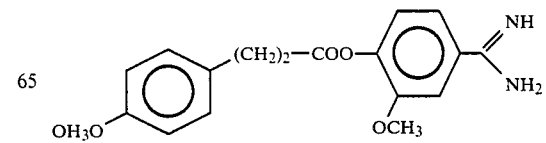

-continued

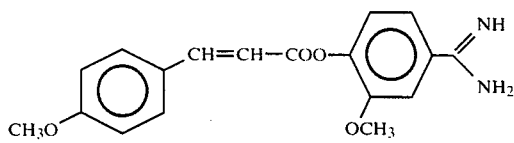

EXAMPLE 27

Synthesis of 4-amidino-2-benzoylphenyl 4-benzyloxybenzoate

Compound No. 45

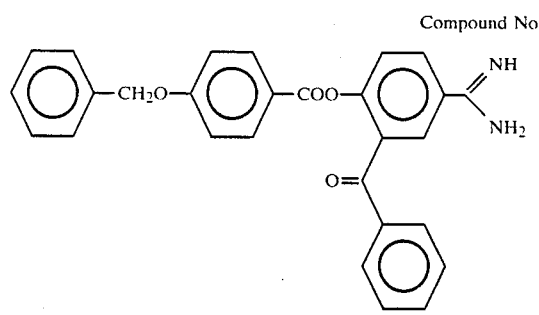

To a mixture of 3.4 g of 4-benzyloxybenzoic acid and 50 ml of dried pyridine, while being cooled in ice, was added 3.7 g of DCC. After having been stirred for 30 minutes, the mixture was admixed with 5.0 g of 4-amidino-2-benzoylphenol methanesulfonate and stirred overnight at room temperature. The reaction mixture was freed from the insolubles by filtration and mixed with ethyl ether. The precipitated insoluble substance was recrystallized from a methanol-ethyl ether mixture to obtain 5.2 g of colorless crystals of 4-amidino-2-benzoylphenyl 4-benzoyloxybenzoate methanesulfonate.

EXAMPLE 28

Synthesis of 4-amidino-2-benzoylphenyl 4-hydroxybenzoate

Compound No. 46

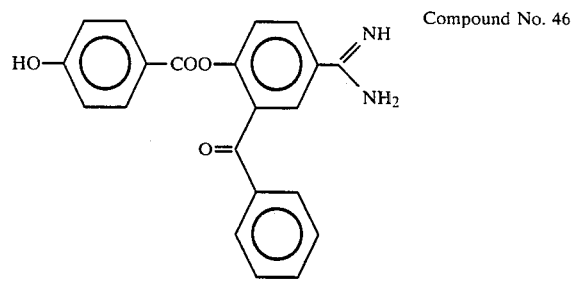

To 25 ml of acetic acid, was added 2.7 g of 4-amidino-2-benzoylphenyl 4-benzyloxybenzoate methanesulfonate followed by 1 ml of anisole. To the mixture cooled in ice, was added 13.5 g of a 30% solution of hydrogen bromide in acetic acid. The mixture was stirred for 5 hours and mixed with ethyl ether. The precipitate was collected by filtration and recrystallized from a methanol-ethyl ether mixture to obtain 1.4 g of 4-amidino-2-benzoylphenyl 4-hydroxybenzoate hydrobromide.

EXAMPLE 29b

Synthesis of 4-amidino-2,6-dibromophenyl 3,4-methylenedioxybenzoate

Compound No. 47

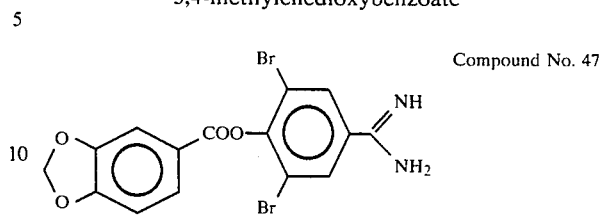

To a solution of 5 g of 4-amidino-2,6-dibromophenol in 100 ml of pyridine, while being cooled in ice and stirred, was added 2.4 g of piperonyl chloride. The mixture was stirred for 30 minutes while being cooled in ice, then for 3 hours at room temperature, and mixed with about 300 cc of ethyl ether. The precipitate which was formed was collected by filtration and recrystallized from ethanol to obtain 4.8 g of colorless crystals of 4-amidino-2,6-dibromophenyl 3,4-methylenedioxybenzoate methanesulfonate.

EXAMPLE 29b

The 4-amidino-2,6-dibromophenol methanesulfonate employed above was obtained in the following manner:

To a solution of 5.2 g of 4-amidinophenol hydrochloride in 100 ml of water, while being stirred, was added dropwise 9.6 g of bromine (Br$_2$). After 3 hours of stirring at room temperature, a saturated aqueous sodium bicarbonate solution and an aqueous sodium thiosulfate solution were added to the reaction mixture. The crystals which were precipitated were collected by filtration, suspended in ethanol, and mixed with methanesulfonic acid. The suspension once turned into a clear solution but soon white crystals separated out of the solution. The crystals were collected by filtration and recrystallized from ethanol to obtain 6.4 g of colorless crystals of 4-amidino-2,6-dibromophenol.

mp: 215°–217° C.

IR, $\nu_{max}^{KBr}$, cm$^{-1}$: 3650–2500, 1690, 1630, 1455.

NMR, DMSO-d$_6$, δ: 2.49 (3H, s), 8.13 (2H, s), 9.03–9.46 (4H, br).

EXAMPLE 30

The following compounds were obtained by the procedures similar to those of Examples 15 to 25 and 29:

Compound No. 48

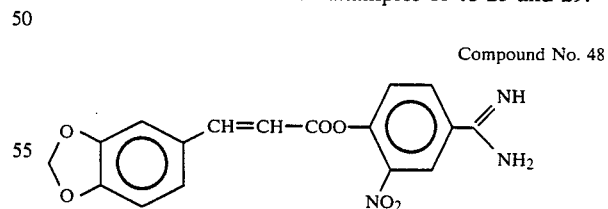

Compound No. 49

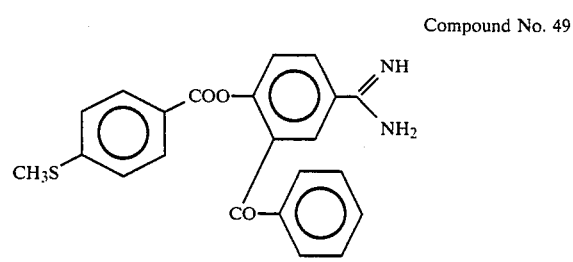

-continued

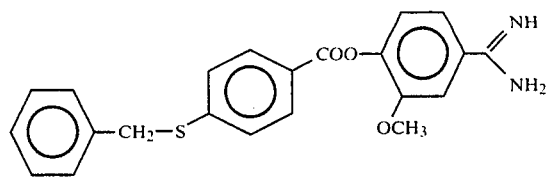

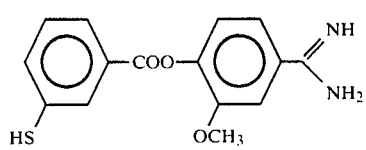

Compound No. 50

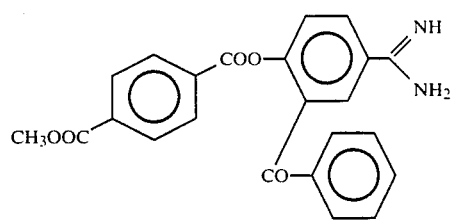

Compound No. 51

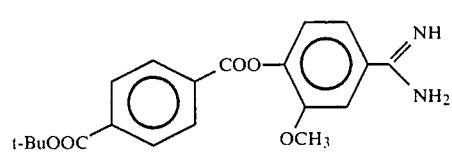

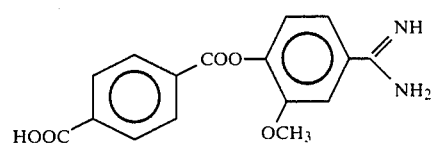

Compound No. 52

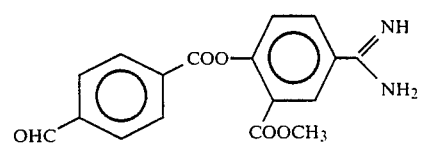

Compound No. 53

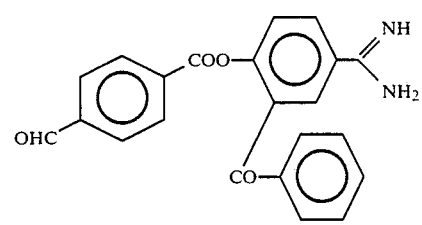

-continued

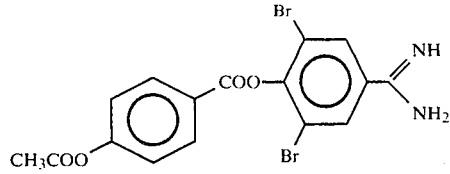

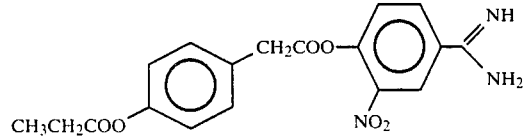

EXAMPLE 31

Synthesis of 4-amidino-2-benzoylphenyl 4-acetyloxycinnamate

Compound No. 54

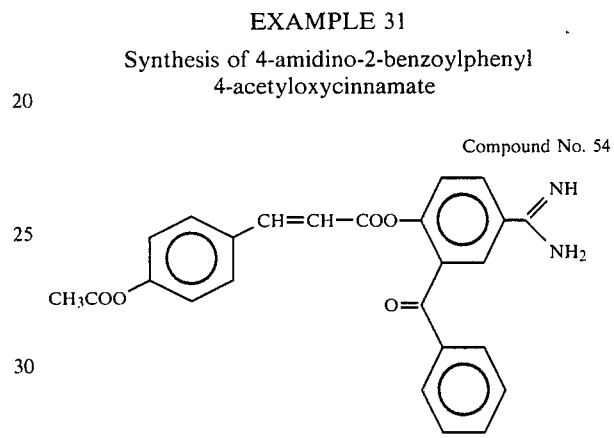

To a mixture of 3.1 g of 4-acetyloxycinnamic acid and 50 ml of dried pyridine, while being cooled in ice, was added 3.7 g of DDC. To the mixture, after having been stirred for 30 minutes, was added 5.0 g of 4-amidino-2-benzoylphenol methanesulfonate. The mixture was stirred overnight at room temperature. The insolubles precipitated from the reaction mixture were collected by filtration and mixed with DMF. Ethyl ether was added to the supernatant to precipitate an insoluble substance which was recrystallized from ethanol, yielding 4.7 g of colorless crystals of 4-amidino-2-benzoylphenyl 4-acetyloxycinnamate methanesulfonate.

EXAMPLE 32

Synthesis of 4-amidino-2-benzoylphenyl 3-(4-acetyloxy)phenylpropionate

Compound No. 55

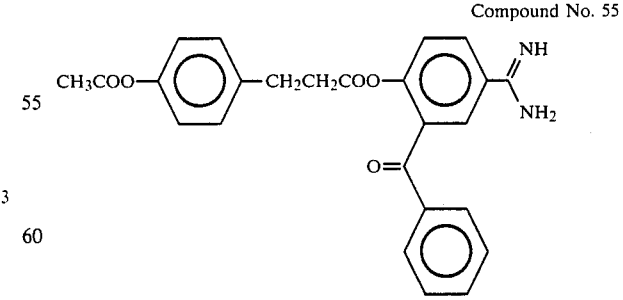

The catalytic reduction of 2.6 g of 4-amidino-2-benzoylphenyl 4-acetyloxyphenylcinnamate methaanesulfonate was carried out in 25 ml of DMF using 500 mg of a 10% palladium-carbon. The reaction mixture was freed from the palladium-carbon by filtration and mixed

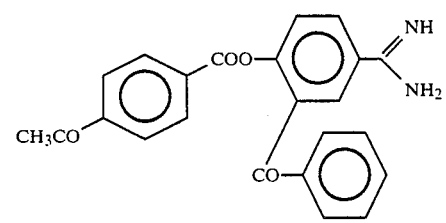

with ethyl ether. The precipitate which was formed was recrystallized from a methanol-ethyl ether mixture to obtain 1.01 g of colorless crystals of 4-amidino-2-benzoylphenyl 3-(4-acetyloxy)phenylpropionate methanesulfonate.

EXAMPLE 33

Synthesis of 4-amidino-2-benzoylphenyl 4-acetylaminobenzoate

Compound No. 56

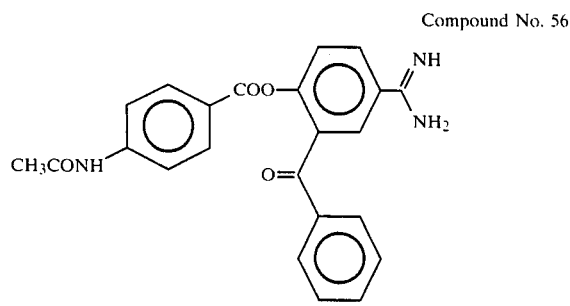

To a solution of 1.79 g of 4-acetylaminobenzoic acid in 50 ml of dried pyridine, was added 3.1 g of DCC. The mixture was stirred for 30 minutes while being cooled in ice. After addition of 3.36 g of 4-amidino-2-benzoylphenol methanesulfonate, the mixture was further stirred overnight. The reaction mixture was removed of the insolubles and mixed with ethyl ether to obtain a colorless solid substance which on recrystallization from methanol yielded 0.9 g of colorless crystals of 4-amidino-2-benzoylphenyl 4-acetylaminobenzoate methanesulfonate.

EXAMPLE 34

Synthesis of 4-amidino-2-methoxyphenyl 4-benzyloxycarbonylaminomethylbenzoate

Compound No. 57

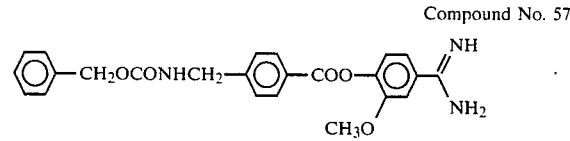

To a solution of 3.7 g of 4-benzyloxycarbonylaminomethylbenzoic acid in 40 ml of dried pyridine, was added 3.1 g of DCC with cooling in ice. The mixture was stirred for 30 minutes. After addition of 3.1 g of 4-amidino-2-methoxyphenol methanesulfonate, the mixture was further stirred overnight at room temperature. The reaction mixture was removed of the insolubles and mixed with ethyl ether to precipitate a colorless solid substance which on recrystallization from a methanol-ethyl ether mixture gave 3.2 g of colorless crystals of 4-amidino-2-methoxyphenyl 4-benzyloxycarbonylaminomethylbenzoate methanesulfonate.

EXAMPLE 35

Synthesis of 4-amidino-2-methoxyphenyl 4-aminomethylbenzoate

Compound No. 58

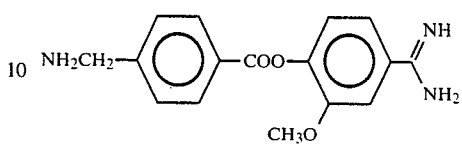

To 1.5 g of 4-amidino-2-methoxyphenyl 4-benzyloxycarbonylaminomethylbenzoate methanesulfonate, was added 15 ml of acetic acid followed by 1 ml of anisole. To the mixture, while being cooled in ice, was added 3.0 ml of an acetic acid solution containing 30% of hydrogen bromide. The mixture was then stirred overnight at room temperature. The insoluble substance precipitated from the reaction mixture was collected by filtration and recrystallization from a methanol-ethyl ether mixture to obtain 1.1 g of colorless crystals of 4-amidino-2-methoxyphenyl 4-aminomethylbenzoate dihydrobromide.

EXAMPLE 36

The following compounds were obtained by the procedures similar to those of Examples 34 and 35:

Compound No. 59

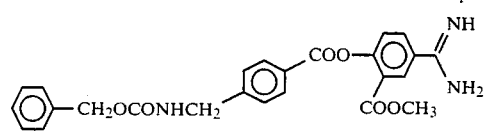

Compound No. 60

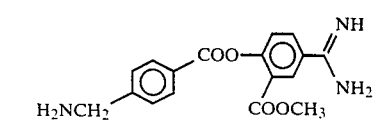

Compound No. 61

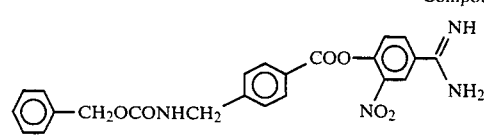

Compound No. 62

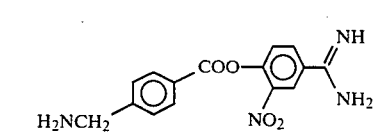

Compound No. 63

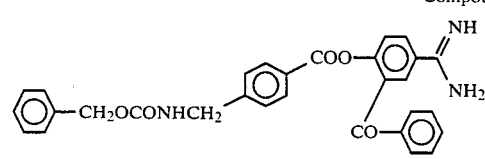

-continued

Compound No. 64

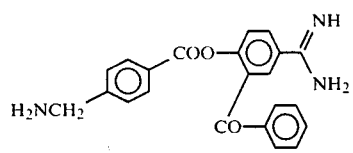

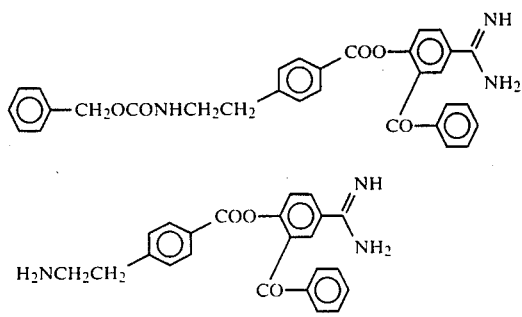

EXAMPLE 37

Synthesis of 4-amidino-2-methoxyphenyl 4-(4-aminophenyl)butyrate

Compound No. 65

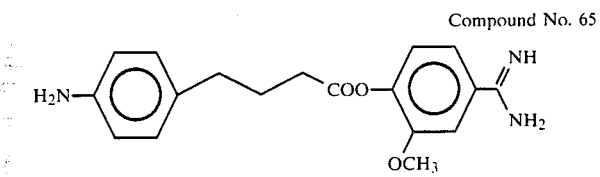

A mixture of 2.4 g of 4-(4-nitrophenyl)butyrate methanesulfonate, 30 ml of dried DMF, 0.5 g of a 10% palladium-carbon, and 0.6 g of methanesulfonic acid was subjected to catalytic reduction. The reaction mixture was freed from the insolubles by filtration and admixed with ethyl ether. The solid substance precipitated from the reaction mixture was collected by filtration, washed with ethyl ether, and recrystallized from ethanol to obtain 1.8 g of a pale yellow powder of 4-amidino-2-methoxyphenyl 4-(4-aminophenyl)butyrate dimethanesulfonate.

EXAMPLE 38

Synthesis of 4-amidino-2-benzoylphenyl 4-dimethylaminobenzoate

Compound No. 66

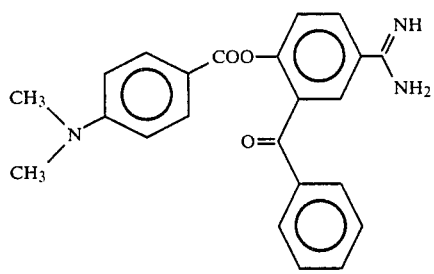

In 50 ml of dried pyridine, was dissolved 1.65 g of 4-dimethylaminobenzoic acid followed by the addition of 3.1 g of DCC. After 30 minutes of stirring, 3.36 g of 4-amidino-2-benzoylphenol methanesulfonate was added to the mixture and the mixture was further stirred overnight. The reaction mixture was removed of the insolubles by filtration and recrystallized from ethanol to yield 1.2 g of 4-amidino-2-benzoylphenyl 4-dimethylaminobenzoate methanesulfonate.

EXAMPLE 39

The following compounds were obtained by the procedures similar to those of Examples 15 to 25, 29, 31 and 32:

Compound No. 67

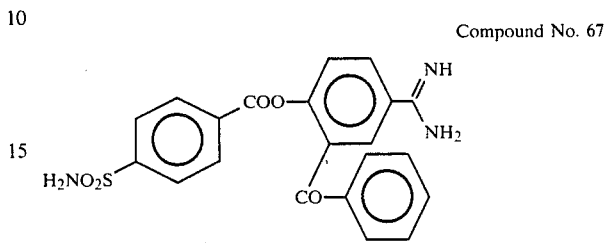

Compound No. 68

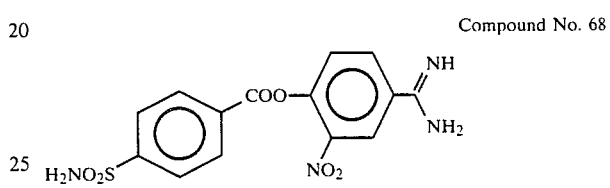

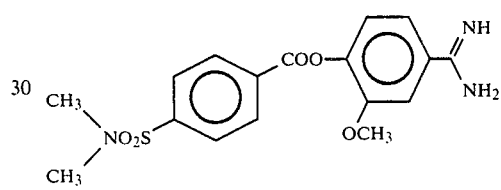

EXAMPLE 40

Synthesis of 4-amidino-2-benzoylphenyl 4-guanidinobenzoate

Compound No. 69

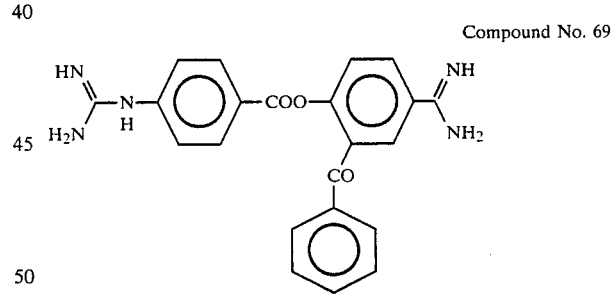

To a solution of 11.6 g of 4-guanidinobenzoic acid hydrochloride in 180 ml of dried pyridine, while being cooled in ice, was added 13.2 g of DCC. After 30 minutes of stirring, 18.0 g of 4-amidino-2-benzoylphenol methanesulfonate was added, and the mixture was further stirred overnight at room temperature. A white solid substance precipitated from the reaction mixture was collected by filtration, washed with acetone, and dissolved in water. The aqueous solution was freed from the water-insoluble DCU by filtration and added to a saturated aqueous sodium bicarbonate solution, while being cooled in ice and stirred. The precipitated pale yellow crystals were collected by filtration, washed with water, then with acetone, and dried to yield 4-amidino-2-benzoylphenyl 4-guanidinobenzoate carbonate.

IR, $v_{max}.^{KBr}$, cm$^{-1}$: 3400, 1730 (shoulder), 1700, 1650, 1600.

While cooling in ice, the carbonate was suspended in 6-fold volume of methanol and to the suspension was added 2.3-fold moles of methanesulfonic acid to turn the suspension into a homogeneous solution. After addition of 40- to 50-fold acetone, triturated to precipitate a white powder which was recrystallized from aqueous acetone to obtain 7.5 g of 4-amidino-2-benzoylphenyl 4-guanidinobenzoate dimethanesulfonate.

EXAMPLE 41

Synthesis of 4-amidino-2-nitrophenyl 4-guanidinobenzoate

Compound No. 70

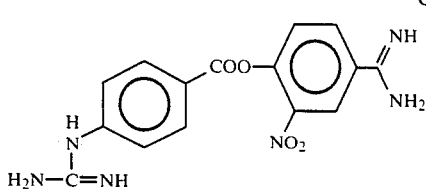

Into 300 ml of dried pyridine, were dissolved 7.0 g of 4-guanidinobenzoyl chloride hydrochloride and 7.4 g of 4-amidino-2-nitrophenol methanesulfonate. The solution was stirred overnight at room temperature. The precipitate which was formed was collected by filtration, suspended in methanol and filtered. The filtrate and 300 ml of ethyl ether was stirred to precipitate a colorless solid substance which was collected by filtration, dissolved in a small volume of methanol, and stirred together with a saturated sodium bicarbonate solution to precipitate the intended carbonate. The precipitated carbonate was collected by filtration, then air-dried, suspended in a small volume of methanol, admixed with methanesulfonic acid at room temperature. After 10 minutes, ethyl ether was added to the reaction mixture to precipitate crystals. The crystals were collected by filtration, washed thoroughly with ethyl ether to obtain 4-amidino-2-nitrophenyl 4-guanidinobenzoate dimethanesulfonate.

mp: 190°–191° C.

IR, $v_{max}.^{KBr}$, cm$^{-1}$: 3330, 3200, 1745, 1680, 1560, 1355, 1175.

EXAMPLE 42

Synthesis of 4-amidino-2-(4-guanidinobenzoylamino)phenyl 4-guanidinobenzoate

Compound No. 73

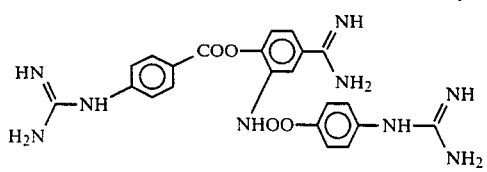

To 50 ml of anhydrous pyridine, was added 4.3 g of 4-guanidinobenzoic acid hydrochloride. To the mixture, while being cooled in ice, was added 4.9 g of DCC. After one hour of stirring, 3.4 g of the 4-amidino-2-aminophenol dimethanesulfonate obtained in Example 23b was added to the mixture and stirred for 30 minutes while being cooled in ice, then overnight at room temperature. After addition of 200 ml of ethyl ether the solvent was removed by decantation. The oily residue was mixed with 200 ml of water and filtered to remove insolubles. The filtrate was mixed with a saturated aqueous sodium bicarbonate solution and the precipitated crystals were collected by filtration to obtain 4-amidino-2-(4-guanidinobenzoylamino)phenyl 4-guanidinobenzoate tricarbonate.

EXAMPLE 43

The following compounds were obtained by the procedures similar to those of Examples 40 to 42:

Compound No. 71

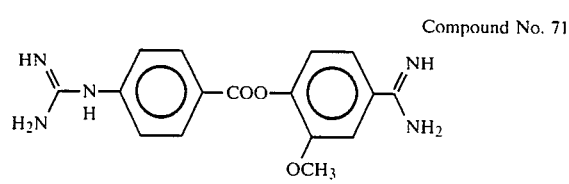

Compound No. 72

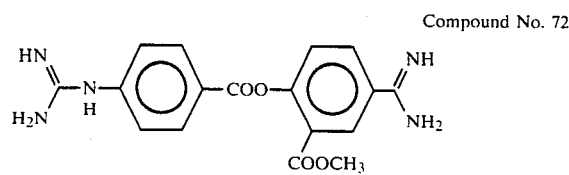

Compound No. 74

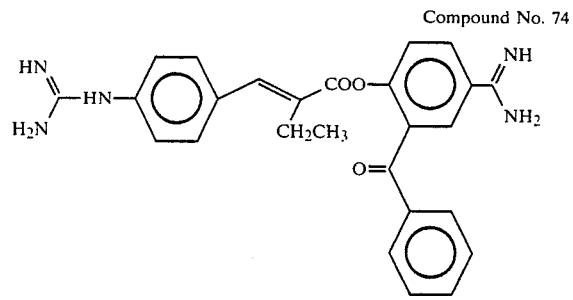

Compound No. 75

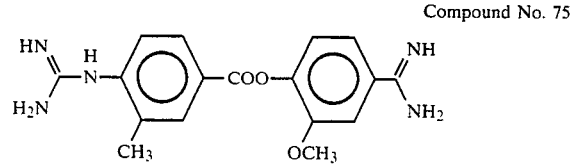

Compound No. 76

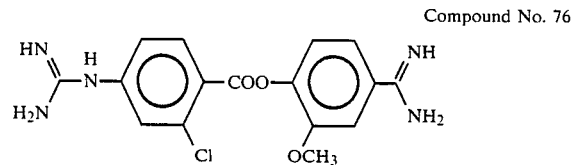

Compound No. 77

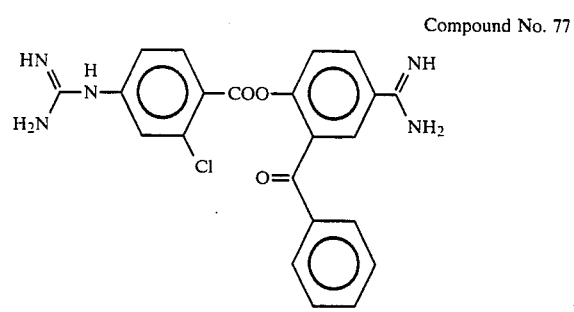

Compound No. 78
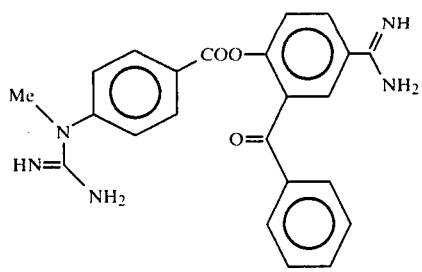
Compound No. 83
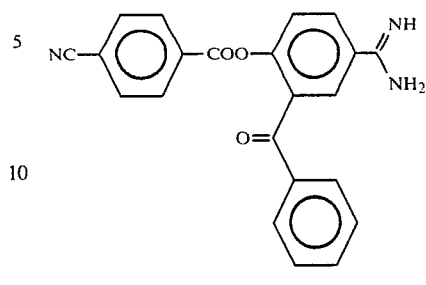
Compound No. 84
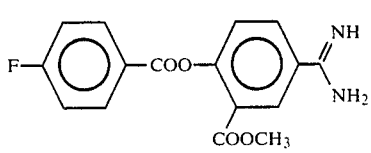
Compound No. 85
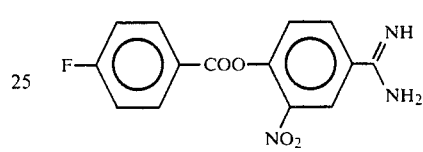
EXAMPLE 44
The following compounds were obtained by the procedures similar to those of Examples 15 to 25, 29, 31 and 32:
Compound No. 79
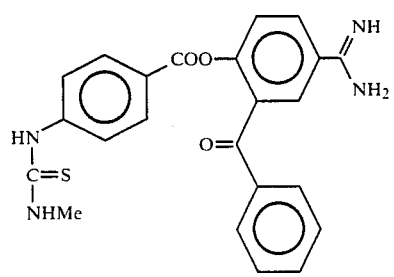
Compound No. 86
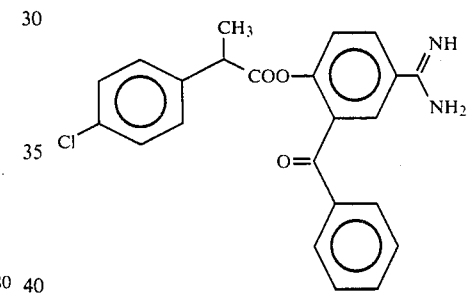
Compound No. 80
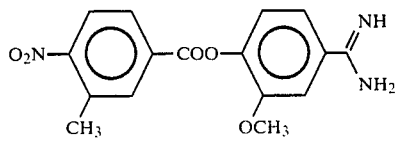
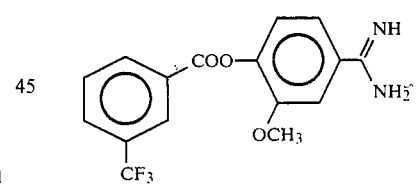
Compound No. 81
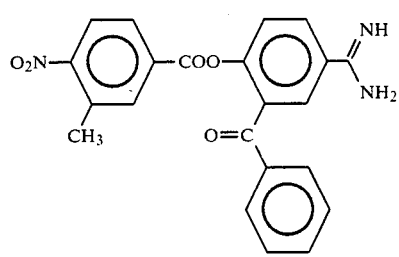
Compound No. 87
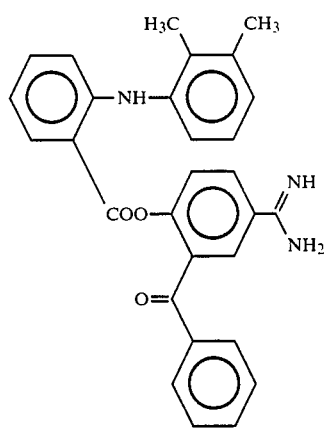
Compound No. 82
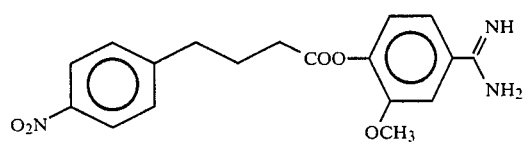

TABLE 5

| Compound No. | Salt | MP (°C.) | IR | NMR |
|---|---|---|---|---|
| 1 | MSA | 159–161 | 3250 3080 1765 1680 1660 | 1.93 (3H, s)<br>2.47 (3H, s)<br>7.37–8.33 (8H, m)<br>9.13–9.70 (4H, br) |
| 2 | MSA | 155–158 | 3360 3050 3000 1745 1670 1525 1350 1190 | 2.38 (3H, s)<br>2.45 (3H, s)<br>7.77 (1H, d, J = 8.5)<br>8.27 (1H, d, d, J = 8.5, 2.0)<br>8.60 (1H, d, J = 2.0)<br>9.23–9.83 (4H, br) |
| 3 | MSA | 173–176 | 3250 3100 2940 1755 1675 | 1.00 (6H, d, J = 6.5)<br>1.60–2.42 (1H, br-m)<br>2.45 (3H, s)<br>2.45 (2H, d, J = 6.5)<br>3.87 (3H, s)<br>7.17–7.67 (3H, m)<br>9.05–9.52 (4H, br) |
| 4 | MSA | 168–170.5 | 3250 3100 2930 1760 1670 | 0.63–1.63 (11H, br-m)<br>1.87–2.47 (2H, br-t)<br>2.42 (3H, s)<br>7.30–8.23 (8H, m)<br>9.07–9.53 (4H, br) |
| 5 | MSA | 154–157 | 3270 3080 1730 1720 1670 1640 1210 | 1.88 (3H, br-d)<br>2.47 (3H, s)<br>3.82 (3H, s)<br>6.13 (1H, d, J = 15.0)<br>6.45 (2H, m)<br>7.25–7.78 (1H, br)<br>7.57 (1H, d, J = 8.5)<br>8.17 (1H, d, d, J = 8.5, 2.0)<br>8.40 (1H, d, J = 2.0)<br>9.22–9.72 (4H, br) |
| 6 | MSA | 139–141 | 3550–2850 1720 1655 1190 | 1.83 (3H, br-d)<br>2.47 (3H, s)<br>5.77 (1H, d, J = 15.0)<br>6.25 (2H, m)<br>6.87–7.40 (1H, m)<br>7.47–8.37 (8H, m)<br>9.20–9.77 (4H, br) |
| 7 | MSA | 278.5–280.5 | 3250 3080 1740 1670 1520 1345 1210 | 1.17 (4H, m)<br>1.77–2.27 (1H, br-m)<br>2.47 (3H, s)<br>7.73 (1H, d, J = 8.5)<br>8.25 (1H, d, d, J = 8.5, 2.0)<br>8.58 (1H, d, J = 2.0)<br>9.20–9.90 (4H, br) |
| 8 | MSA | 158–159 | 3250 3060 1745 1665 | 0.58–1.02 (4H, m)<br>1.32–1.82 (1H, br-m)<br>2.42 (3H, s)<br>7.32–8.25 (8H, m)<br>9.08–9.62 (4H, br) |
| 9 | MSA | 205–208 | 3280 3130 2920 1750 1675 | 1.00–2.93 (11H, br)<br>2.47 (3H, s)<br>3.88 (3H, s)<br>7.17–7.73 (3H, m)<br>9.03–9.60 (4H, br) |
| 10 | MSA | 138–140 | 3270 3070 1755 1675 1210 | 2.17–2.60 (2H, br)<br>2.42 (3H, s)<br>2.90–3.37 (2H, br)<br>5.02 (2H, s)<br>7.03–8.27 (14H, m)<br>9.10–9.67 (4H, br) |
| 11 | 2HBr | | 3600–2400 1760 1670 1655 | |
| 12 | MSA | 153–156 | 3280 3070 1755 1675 1215 | 1.07–1.67 (6H, br)<br>1.97–2.37 (2H, br)<br>2.45 (3H, s)<br>5.03 (2H, s)<br>7.00–8.30 (14H, m)<br>9.17–9.67 (4H, br) |
| 13 | 2HBr | 158–160 | 3500–2700 1765 1680 | 1.07–1.87 (6H, br) |

TABLE 5-continued

| Compound No. | Salt | MP (°C.) | IR | NMR |
|---|---|---|---|---|
| | | | | 2.03–2.43 (2H, br) |
| | | | | 2.50–3.17 (2H, br) |
| | | | | 7.42–8.25 (11H, m) |
| | | | | 8.92–9.25 (2H, br) |
| | | | | 9.37–9.67 (2H, br) |
| 14 | MSA HCl | | 1740 | |
| 15 | MSA HCl | | 1760 | |
| 16 | MSA | 156–157 | 3300 3100 2900 1745 1680 1190 | 0.80–3.10 (12H, br) |
| | | | | 2.43 (3H, s) |
| | | | | 3.87 (3H, s) |
| | | | | 5.02 (2H, s) |
| | | | | 7.08–7.68 (9H, m) |
| | | | | 9.05–9.58 (4H, br) |
| 17 | 2HBr | 197–198.5 | 3450 3300 3100 2970 1750 1675 | 0.82–3.15 (12H, br-m) |
| | | | | 3.92 (3H, s) |
| | | | | 7.22–8.38 (6H, m) |
| | | | | 8.95–9.22 (2H, br) |
| | | | | 9.35–9.65 (2H, br) |
| 18 | MSA | 158–162 | 3320 3100 2900 1740 1725 1675 1200 | 0.83–3.13 (12H, br) |
| | | | | 2.45 (3H, s) |
| | | | | 3.87 (3H, s) |
| | | | | 5.05 (2H, s) |
| | | | | 7.12–7.48 (1H, br) |
| | | | | 7.37 (5H, s) |
| | | | | 7.52 (1H, d, J = 8.5) |
| | | | | 8.12 (1H, d, d, J = 8.5, 2.0) |
| | | | | 8.35 (1H, d, J = 2.0) |
| | | | | 9.08–9.58 (4H, br) |
| 19 | 2HBr | 188–189 | 3400–2800 1758 1730 1670 | 0.80–2.93 (12H, br-m) |
| | | | | 7.47 (1H, d, J = 8.5) |
| | | | | 7.70–8.20 (3H, br) |
| | | | | 8.08 (1H, d, d, J = 8.5, 2.0) |
| | | | | 8.28 (1H, d, J = 2.0) |
| | | | | 8.93–9.20 (2H, br) |
| | | | | 9.37–9.60 (2H, br) |
| 20 | MSA | 168–170 | 3270 3060 1760 1670 1210 | 0.60–3.13 (12H, br) |
| | | | | 2.45 (3H, s) |
| | | | | 5.02 (2H, s) |
| | | | | 6.97–8.30 (14H, m) |
| | | | | 9.03–9.73 (4H, br) |
| 21 | 2HBr | 156–160 | 3500–2600 1750 1680 1665 | 0.73–2.90 (12H, br-m) |
| | | | | 7.40–8.37 (11H, m) |
| | | | | 9.03–9.30 (2H, br) |
| | | | | 9.43–9.70 (2H, br) |
| 22 | MSA | 190–192 | 3350 3100 1732 1660 | 2.42 (6H, br-s) |
| | | | | 7.17–7.97 (6H, m) |
| | | | | 7.97–8.37 (2H, m) |
| | | | | 9.07–9.57 (4H, br) |
| | $H_2CO_3$ | | 3350 2925 2600 1710 1660 1580 | |
| 23 | MSA | 203.5–206 | 3450–2900 1735 1680 1200 | 2.43 (3H, s) |
| | | | | 3.88 (3H, s) |
| | | | | 7.43–7.83 (6H, m) |
| | | | | 8.00–8.27 (2H, m) |
| | | | | 9.07–9.53 (4H, br) |
| 24 | MSA | ~153(d) | 3340 3150 2750 1720 1690 | 2.52 (3H, s) |
| | | | | 7.33–8.57 (8H, m) |
| | | | | 9.07–9.43 (4H, br) |
| 25 | MSA | 191–192 | 3340 3130 1730 1685 1215 | 2.45 (3H, s) |
| | | | | 3.73 (3H, s) |
| | | | | 7.65–7.98 (4H, m) |
| | | | | 8.12–8.42 (3H, m) |
| | | | | 8.53 (1H, d, J = 2.0) |
| | | | | 9.22–9.85 (4H, br) |
| 26 | MSA | 203–205 | 3350 3080 1643 1625 | 2.50 (3H, s) |
| | | | | 7.47–8.40 (8H, m) |
| | | | | 9.17–9.78 (4H, br) |
| 27 | MSA | 232–235 | 3450 3350 3050 1715 1615 1540 1350 1215 | 2.47 (3H, s) |
| | | | | 7.60–8.48 (7H, m) |
| | | | | 8.70 (1H, d, J = 2.0) |
| | | | | 9.24–9.85 (4H, br) |
| 28 | | >300 | 3400–3000 1745 1685 1235 | |
| 29 | MSA | ~160 | 3275 3100 1730 1675 1650 | 2.48 (3H, s) |
| | | | | 7.25–8.38 (13H, m) |
| | | | | 9.17–9.76 (4H, br) |
| 30 | MSA | 233–234 | 3400–2800 1738 1660 1220 | 2.48 (3H, s) |
| | | | | 7.33–8.26 (13H, m) |
| | | | | 8.96–9.53 (4H, br) |
| | | | | 10.36 (1H, s) |

TABLE 5-continued

| Compound No. | Salt | MP (°C.) | IR | NMR |
|---|---|---|---|---|
| 31 | MSA | 205~ | 3270 3080 1725 1660 1635 1210 | 2.50 (3H, s)<br>3.93 (3H, s)<br>6.90 (1H, d, J = 16.0)<br>7.33-8.13 (9H, m)<br>9.13-9.60 (4H, br) |
| 32 | MSA | 158-160 | 3360 3140 1770 1710 1680 1495 1210 | 2.40 (3H, s)<br>2.95 (4H, s)<br>3.82 (3H, s)<br>7.27 (7H, br-s)<br>7.53 (1H, s)<br>8.97-9.43 (4H, br) |
| 33 | MSA | 173-175 | 3250 3095 1765 1690 1685 1220 1110 | 1.33-2.67 (6H, m)<br>2.38 (3H, s)<br>7.00-8.27 (13H, br)<br>9.07-9.60 (4H, br) |
| 34 | MSA | 176-180 | 3500-2800 1745 1665 1220 1180 | |
| 35 | MSA | 185-189 | 3300 3120 1730 1680 1205 | |
| 36 | MSA | 93-95 | 3250 3030 1720 | |
|  | H$_2$SO$_4$ | 100-103 | 3700-2600 1750 1690 | 2.43 (3H, s)<br>8.42-10.68 (m) |
| 37 | MSA | 220-222 | 3400-2900 1750 1690 1250-1150 | 2.50 (6H, s)<br>7.50 (2H, d, J = 8.0)<br>7.97 (1H, d, J = 8.0)<br>8.12 (2H, d, J = 8.0)<br>8.42 (1H, d, d, J = 5.0, 2.0)<br>8.75 (1H, d, J = 2.0)<br>9.37-9.95 (4H, br) |
| 38 | MSA | 179-180 | 3090 2950 1735 1680 1608 1350 1230 1180 | |
| 39 | MSA | 187-188 | 3400-2950 1740 1670 1210 1180 | 1.27 (9H, s)<br>2.50 (3H, s)<br>7.20-8.43 (12H, m)<br>9.10-10.00 (4H, br) |
| 40 | MSA | 134-136 | 3500-2900 1765 1675 1210 | 0.85 (6H, d, J = 6.0)<br>1.23 (3H, d, J = 7.0)<br>2.45 (3H, s)<br>7.00-8.17 (12H, m)<br>8.87-9.53 (4H, br) |
| 41 | MSA | 104-107 | 3450-2650 1741 1613 1200 | 2.45 (3H, s)<br>3.73 (3H, s)<br>8.43-9.90 (12H, m)<br>9.13-9.63 (4H, br) |
| 42 | MSA | 192-194 | 3300 3100 1740 1685 1660 1205 1170 | 2.47 (3H, s)<br>3.80 (3H, s)<br>6.95 (2H, d, J = 9.0)<br>7.23-8.50 (10H, m)<br>8.75-9.72 (4H, br) |
| 43 | MSA | 153-154 | 3270 3100 1765 1685 1490 1220 | 2.40 (3H, s)<br>3.75 (3H, s)<br>3.83 (3H, s)<br>3.97 (2H, s)<br>6.70-7.60 (7H, m)<br>8.98-9.45 (4H, br) |
| 44 | MSA | 181-183 | 3600-2750 1730 1680 1280-1140 | 0.70-2.05 (7H, m)<br>2.50 (3H, s)<br>4.13 (2H, q, J = 6.0)<br>7.16 (2H, d, J = 9.0)<br>7.73-8.58 (4H, m)<br>8.72 (1H, d, J = 2.0)<br>9.22-10.02 (4H, br) |
| 45 | MSA | 132-134 | 3300 3100 1750 1670 1600 1460 1445 1250 | 2.47 (3H, s)<br>5.20 (2H, s)<br>6.97-8.60 (17H, br)<br>9.40-10.13 (4H, br) |
| 46 | HBr | 202-204 | 3300 3100 1715 1660 1605 1275 1210 | 6.80 (2H, d, J = 8.0)<br>7.27-8.47 (10H, m)<br>8.70-9.80 (5H, br) |
| 47 | MSA | 255-258 | 3600-2750 1740 1690 1440 | 2.47 (3H, s)<br>6.25 (2H, s)<br>7.18 (1H, d, J = 8.0)<br>7.62 (1H, d, J = 1.5)<br>7.87 (1H, d, d, J = 8.0, 1.5)<br>8.28 (2H, s)<br>9.23-9.72 (4H, br) |
| 48 | MSA | 176-179 | 3300 3100 1725 1690 1620 1530 1450 1350 1230 | 2.53 (3H, s)<br>6.10 (2H, s)<br>6.47-8.70 (11H, m)<br>9.20-10.03 (4H, br) |

TABLE 5-continued

| Compound No. | Salt | MP (°C.) | IR | NMR |
|---|---|---|---|---|
| 49 | MSA | 200-202 | 3270 3100 1725 1660 1588 1173 | 2.43 (3H, s)<br>2.47 (3H, s)<br>7.18-8.28 (12H, m)<br>9.18-9.65 (4H, br) |
| 50 | MSA | 175-177 | 3400-2900 1750 1720 1700 1665 1210 | 2.43 (3H, s)<br>7.20-8.48 (12H, m)<br>9.03-9.90 (4H, br) |
| 51 | MSA | 165-170 | 3600-2900 1750 1730 1690 1200 | 2.45 (3H, s)<br>3.75 (3H, s)<br>7.75 (2H, d, J = 8.0)<br>7.95-8.62 (5H, m)<br>9.12-9.95 (4H, br)<br>10.17 (1H, s) |
| 52 | MSA | 164-165 | 3250 3050 1755 1705 1670 1210 | 2.43 (3H, s)<br>7.33-8.30 (12H, br)<br>9.07-9.60 (4H, br)<br>10.00 (1H, s) |
| 53 | P—TsOH | 100-106 | 3500-2900 1740 1660 1210 | |
| 54 | MSA | 144-146 | 3350 3050 1765 1725 1665 1625 1475 1310 | 2.30 (3H, s)<br>2.50 (3H, s)<br>6.53 (1H, d, J = 16.0)<br>7.17-8.30 (13H, br)<br>9.10-9.87 (4H, br) |
| 55 | MSA | 167-169 | 3500 3200 1760 1740 1690 1670 1480 1310 | 2.27 (3H, s)<br>2.43 (3H, s)<br>2.37-2.73 (4H, m)<br>6.93-8.27 (12H, m)<br>9.14-9.81 (4H, br) |
| 56 | MSA | 241-243 | 3260 3050 1740 1680 1600 1205 1180 | 2.10 (3H, s)<br>2.43 (3H, s)<br>7.63 (br-s)<br>8.10 (1H, s)<br>9.10-9.67 (4H, br)<br>10.37 (1H, s) |
| 57 | MSA | 157-159 | 3300 1735 1670 1540 1495 1255 1200 | 2.43 (3H, s)<br>3.87 (3H, s)<br>4.33 (2H, d, J = 5.0)<br>5.03 (2H, s)<br>7.30-8.10 (12H, br)<br>8.93-9.53 (4H, br) |
| 58 | 2HBr | 229-231 | 3250 3100 1745 1665 1590 1480 1255 1230 | 3.93 (3H, s)<br>4.23 (2H, J = 5.0)<br>7.57-8.27 (5H, m)<br>8.34-8.81 (2H, br)<br>8.94-9.67 (4H, br) |
| 59 | MSA | 137-139 | 3300 3100 1730 1680 1540 1310 1255 | |
| 60 | 2HBr | 204-206 | 3550 3200 1750 1730 1670 1480 1430 1260 1220 | 3.43 (3H, s)<br>3.73 (3H, s)<br>6.35 (2H, d, J = 5.0)<br>7.67-8.80 (9H, m)<br>9.03-9.93 (4H, br) |
| 61 | MSA | 150-152 | 3350 3100 1745 1680 1530 1350 1260 1230 | 2.47 (3H, s)<br>4.37 (2H, d, J = 5.0)<br>5.07 (2H, s)<br>7.33-8.66 (12H, br)<br>9.19-9.89 (4H, br) |
| 62 | 2HBr | 215-218 | 3050 1760 1670 1540 1355 1220 | |
| 63 | MSA | 102-104 | 3250 3050 1740 1610 1470 1445 1315 1260 | |
| 64 | 2HBr | | 3300 3100 1745 1670 1640 1470 1320 1220 | |
| 65 | 2MSA | 165-168 | 3500-2600 1760 1705 1690 1210 | 1.63-3.15 (6H, m)<br>2.50 (3H, s)<br>3.93 (3H, s)<br>7.20-7.93 (9H, m)<br>9.02-9.77 (4H, br) |
| 66 | MSA | 190-194(d) | 3250 3080 1730 1665 1602 1165 | 2.40 (3H, s)<br>2.94 (6H, s)<br>6.55 (2H, d, J = 8.0)<br>7.33-8.27 (10H, m)<br>9.00-9.57 (4H, br) |
| 67 | MSA | 181-187 | 3550-2900 1730 1660 1200 | 2.43 (3H, s)<br>7.23-8.50 (14H, m)<br>9.03-9.83 (4H, br) |
| 68 | MSA | 183-187 | 3500-2800 1760 1710 1220 1160 | |
| 69 | $H_2CO_3$ | | 3400 1730 1700 1650 | |

TABLE 5-continued

| Compound No. | Salt | MP (°C.) | IR | NMR |
|---|---|---|---|---|
| | 2MSA | 220–224 | 1600 3500–2900 1740 1655 1605 1210 1185 1040 | 2.47 (6H, s) 7.27–8.37 (16H, m) 9.12–9.62 (4H, br) 10.23 (br-s) |
| 70 | 2MSA | 190–191 | 3330 3200 1745 1680 1560 1355 1175 | |
| 71 | 2MSA | 218–220 | 3300 3150 1730 1675 1265 1210 1180 | 2.50 (6H, s) 3.90 (3H, s) 7.27–8.33 (11H, m) 9.07–9.60 (4H, br) 10.28 (1H, br-s) |
| 72 | MSA HCl | 141(d) | 3650–2500 1745 1720 1680 1600 1265 1230 1185 | 2.52 (3H, s) 3.78 (3H, s) 7.33–8.58 (11H, m) 9.32–9.95 (4H, br) 10.82 (1H, br) |
| 73 | $3H_2CO_3$ | 85~(d) | 3700–2400 1720 1660 1605 | |
| 74 | 2MSA | | 3300 3100 1720 1660 1200 | |
| 75 | 2MSA | 222–227 | 3500–3000 1740 1690 1210 1170 | 2.37 (3H, s) 2.50 (6H, s) 3.92 (3H, s) 7.20–8.43 (10H, m) 9.02–9.62 (4H, br) 9.78 (1H, br) |
| 76 | 2-PTsOH | | 3550–2850 1750 1680 1190 | |
| 77 | 2-PTsOH | 120~(d) | 3500–2900 1750 1670 1200 | |
| 78 | MSA HCl | 101–102(d) | 3300 3150 1715 1670 1585 1190 | |
| 79 | MSA | 83–84(d) | 3250 3050 1740 1665 1205 | |
| 80 | MSA | 204–207 | 3300 3100 1755 1680 1205 1170 | 2.45 (3H, s) 2.60 (3H, s) 3.92 (3H, s) 7.57 (1H, s) 7.63 (2H, d, J = 7.0) 8.17 (1H, s) 8.22 (2H, d, J = 6.0) 9.02–9.75 (4H, br) |
| 81 | MSA | 178–180 | 3400–2900 1750 1670 1220 1210 | 2.50 (3H, s) 7.27–8.57 (11H, m) 9.05–9.97 (4H, br) |
| 82 | MSA | 136–137 | 3450–3000 1765 1690 1210 | 1.67–3.20 (6H, m) 2.47 (3H, s) 3.88 (3H, s) 7.27–7.73 (5H, m) 8.17 (2H, d, J = 8.0) 8.98–9.75 (4H, br) |
| 83 | MSA | 183–186 | 3500–3000 2250 1760 1740 1675 1220 | 2.47 (3H, s) 7.30–8.55 (12H, m) 9.15–9.85 (4H, br) |
| 84 | MSA | 186–188 | 3600–2900 1740 1730 1680 1220 | 2.52 (3H, s) 3.78 (3H, s) 7.27–8.75 (7H, m) 9.25–9.95 (4H, br) |
| 85 | MSA | 123–125 | 3400 3100 1750 1690 1200 | 2.47 (3H, s) 7.23–8.40 (7H, m) 8.58–9.07 (4H, br) |
| 86 | MSA | 143–144 | 3400–2800 1750 1660 1200 | 1.25 (3H, d, J = 7.0) 2.45 (3H, s) 6.98–8.18 (12H, m) 8.88–9.51 (4H, br) |
| 87 | MSA | 210–212 | 3330 3050 1690 1670 1570 1500 1315 1270 | |

What is claimed is:

1. An amidino compound or a pharmaceutically acceptable acid addition salt thereof, said amidino compound being represented by the formula

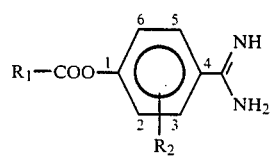

wherein $R_1$ represents a straight or branched chain alkyl group of 1 to 6 carbon atoms, a straight or branched chain alkenyl group of 2 to 6 carbon atoms including 1 to 3 double bonds, $R_3$—$(CH_2)_a$—, $R_4$—$(CH_2)_b$—,

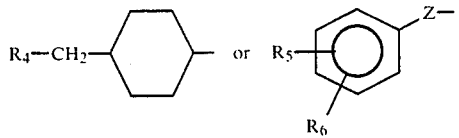

where $R_3$ is cycloalkyl group of 3 to 6 carbon atoms or cycloalkenyl group of 3 to 6 carbon atoms including 1 to 2 double bonds; a is 0, 1, 2 or 3; $R_4$ is amino or guanidino group possessing radical protecting group or not; b is a number of 1 to 5; $R_5$ and $R_6$, which may be the same or different, are each a hydrogen atom, straight or branched alkyl group of 1 to 4 carbon atoms, —$OR_7$, methylenedioxy group, —$SR_7$, —$COOR_7$, —$COR_8$, —$OCOR_9$, —$NHCOR_9$,

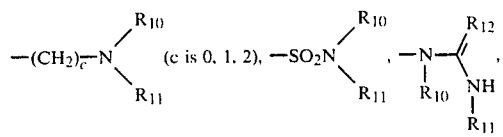

$NO_2$, CN, halogen atom, —$CF_3$, or

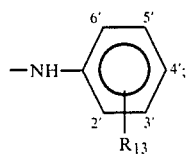

$R_7$ is hydrogen atom, straight or branched alkyl group of 1 to 4 carbon atoms or benzyl group; $R_8$ is hydrogen atom, straight or branched alkyl group of 1 to 4 carbon atoms; $R_9$ is straight or branched alkyl group of 1 to 4 carbon atoms; $R_{10}$ and $R_{11}$, which may be the same or different, are each a hydrogen atom, straight or branched alkyl group of 1 to 4 carbon atoms, or amino radical protecting group; $R_{12}$ is O, S, or NH; $R_{13}$ is 2',3'-dimethyl or 3'-$CF_3$ group; Z is —$(CH_2)_d$— (d is 0, 1, 2 or 3),

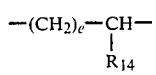

(e is 0, 1 or 2) or

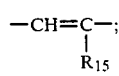

$R_{14}$ is straight or branched alkyl group of 1 to 4 carbon atoms; $R_{15}$ is hydrogen atom, straight or branched alkyl group of 1 to 4 carbon atoms; $R_2$ represents —$OR_{16}$, —$COOR_{16}$, halogen atom, —$NO_2$,

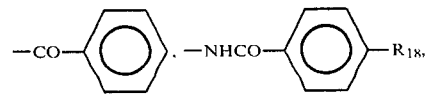

wherein $R_{16}$ is straight or branched alkyl group of 1 to 4 carbon atoms; and $R_{18}$ is hydrogen atom or guanidino group;

wherein said protecting group is an amino or guanidino radical protecting group selected from the group consisting of t-butoxycarbonyl, benzyloxycarbonyl, acetyl, benzoyl, tosyl, nitro, benzyl and t-butyl groups.

2. An amidino compound and a pharmaceutically acceptable acid addition salt thereof according to claim 1, wherein $R_2$ is 2-$OCH_3$, 2-$COOCH_3$, 2-chloro, 2-$NO_2$,

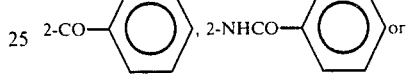

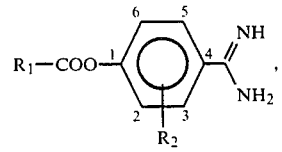

3. An anti-complement agent comprising as an active ingredient an amidino compound, or a pharmaceutically acceptable acid addition salt thereof, represented by the formula

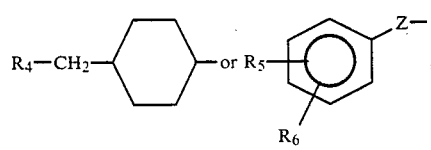

wherein $R_1$ represents a straight or branched chain alkyl group of 1 to 6 carbon atoms, a straight or branched chain alkenyl group of 2 to 6 carbon atoms including 1 to 3 double bonds, $R_3$—$(CH_2)_a$—, $R_4$—$(CH_2)_b$—,

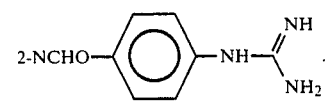

where $R_3$ is cycloalkyl group of 3 to 6 carbon atoms or cycloalkenyl group of 3 to 6 carbon atoms including 1 to 2 double bonds; a is 0, 1, 2 or 3; $R_4$ is amino or guanidino group possessing radical protecting group or not; b is a number of 1 to 5; $R_5$ and $R_6$, which may be the same or different, are each a hydrogen atom, straight or branched alkyl group of 1 to 4 carbon atoms, —$OR_7$, methylenedioxy group, —$SR_7$, —$COOR_7$, —$COR_8$, —$OCOR_9$, —$NHCOR_9$,

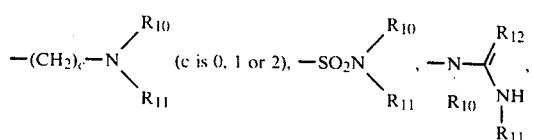

NO₂, CN, halogen atom, —CF₃ or

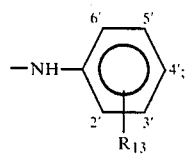

$R_7$ is hydrogen atom, straight or branched alkyl group of 1 to 4 carbon atoms or benzyl group; $R_8$ is hydrogen atom, straight or branched alkyl group of 1 to 4 carbon atoms; $R_9$ is straight or branched alkyl group of 1 to 4 carbon atoms; $R_{10}$ and $R_{11}$, which may be the same or different, are each a hydrogen atom, straight or branched alkyl group of 1 to 4 carbon atoms, or amino radical protecting group; $R_{12}$ is O, S or NH; $R_{13}$ is 2′,3′-dimethyl or 3′-CF₃ group; Z is —(CH₂)₃— (d is 0, 1, 2 or 3),

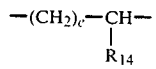

(e is 0, 1 or 2) or

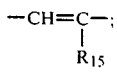

$R_{14}$ is straight or branched alkyl group of 1 to 4 carbon atoms; $R_{15}$ is hydrogen atom, straight or branched alkyl group of 1 to 4 carbon atoms; $R_2$ represents —OR₁₆, —COOR₁₆, halogen atom, —NO₂,

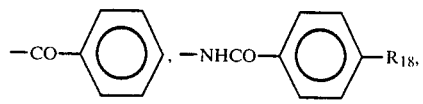

wherein $R_{16}$ is straight or branched alkyl group of 1 to 4 carbon atoms; and $R_{18}$ is hydrogen atom or guanidino group;

wherein said protecting group is an amino or guanidino radical protecting group selected from the group consisting of t-butoxycarbonyl, benzyloxycarbonyl, acetyl, benzoyl, tosyl, nitro, benzyl and t-butyl groups.

4. An anticomplement agent comprising as an active ingredient an amidino compound or a pharmaceutically acceptable acid addition salt thereof according to claim 3, wherein R₂ is 2-OCH₃, 2-COOCH₃, 2-chloro, 2-NO₂,

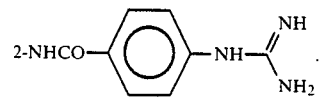

* * * * *